United States Patent
Allersma et al.

(10) Patent No.: US 11,162,110 B2
(45) Date of Patent: Nov. 2, 2021

(54) TOMATO PLANTS WITH IMPROVED DISEASE RESISTANCE

(71) Applicant: SEMINIS VEGETABLE SEEDS, INC., St. Louis, MO (US)

(72) Inventors: Anton P. Allersma, Berkel en Rodenrijs (NL); Derek R. Drost, Penn Valley, CA (US); James D. Frantz, Cape Coral, FL (US); Laura Gallegos, St. Louis, MO (US); Susana García Andrés, Almería (ES); Elaine Graham, Davis, CA (US); Stephanie Pedroni, St. Louis, MO (US); Maria B. Salleres Neira, St. Louis, MO (US)

(73) Assignee: Seminis Vegatable Seeds, Inc., St. Louis, MO (US)

( * ) Notice: Subject to any disclaimer, the term of this patent is extended or adjusted under 35 U.S.C. 154(b) by 0 days.

(21) Appl. No.: 16/516,032

(22) Filed: Jul. 18, 2019

(65) Prior Publication Data
US 2020/0048655 A1 Feb. 13, 2020

Related U.S. Application Data

(60) Provisional application No. 62/701,305, filed on Jul. 20, 2018, provisional application No. 62/815,622, filed on Mar. 8, 2019.

(51) Int. Cl.
*C12N 15/82* (2006.01)
*A01H 6/82* (2018.01)

(52) U.S. Cl.
CPC .................. *C12N 15/8282* (2013.01)

(58) Field of Classification Search
None
See application file for complete search history.

(56) References Cited

U.S. PATENT DOCUMENTS

2009/0126037 A1   5/2009   Finkers et al.
2014/0123332 A1   5/2014   Verhoeff et al.

FOREIGN PATENT DOCUMENTS

CN    106811462        6/2017
WO    99/05903 A1      2/1999
WO    WO2018219941 A1  12/2018

OTHER PUBLICATIONS

Bashi, et al., "Resistance in Tomatoes to *Stemphylium floridanum* and *S. botryosum* f. sp. Lycopersici" Phytopathology, (1972), 1542-1544, 63.

Behare, et al. Restriction Fragment Length Polymorphism Mapping of the Stemphylium Resistance Gene in Tomato, Molecular Plant-Microbe Interactions, (1991), pp. 489-492, 4-5.

Foolad and Panthee, "Marker-Assisted Selection in Tomato Breeding," Critical Reviews in Plant Sciences, (2012), 93-123, 31-2.

Hanson, et al., "Conventional and Molecular Marker-Assisted Selection and Pyramiding of Genes for Multiple Disease Resistance in Tomato," Scientia Horticulturae, (2016), 346-354, 201.

Hendrix and Frazier, Studies on the Inheritance of Stemphylium Resistance in Tomatoes, University of Hawaii Agricultural Experiment Station, (1949), 5-24, Technical Bulletin No. 8.

Maayan et al., "Using genomic analysis to identify tomato Tm-2 resistance-breaking mutations and their underlying evolutionary path in a new and emerging tobamovirus" Archives of Virology, (2018), pp. 1863-1875, 163.

Perl-Treves, et al., "Genetic Mapping of Tomato eDNA Clones Encoding the Chloroplastic and the Cytosolic Isozymes of Superoxide Dismutase," Biochemical Genetics, (1990), 543-552, 28-9/10.

Salem, et al., "A New Tobamovirus Infecting Tomato Crops in Jordan," Archives of Virology, (2016), 503-506, 161-2.

Sato, et al., "The Tomato Genome Sequence Provides Insights Into Fleshy Fruit Evolution, The Tomato Genome Consortium," Nature, (2012), 635-641, 485.

Sauer et al., "Oligonucleotide-Mediated Genome Editing Provides Precision and Function to Engineered Nucleases and Antibiotics in Plants," Plant Physiology, (2016), 1917-1928, 170-4.

Scott and Ji, "A Caps Marker Linked to the Tomato Gray Leafspot (*Stemphyllium* sp.) Resistance Gene Sm," Research Reports—TGC Report, (2009), 29-31, 59, University of Florida, Wimauma, FL, USA.

Yang, et al., "Mapping and Screening of the Tomato Stemphylium Lycopersici Resistance Gene, Sm, Based on Bulked Segregant Analysis in Combination with Genome Resequencing," BMC Plant Biology (2017), 1-10, 17-266.

Invitation to Pay Additional Fees regarding PCT Application No. PCT/US2019/042388, mailed Oct. 1, 2019, 3 pages.

International Search Report and Written Opinion regarding PCT Application No. PCT/US2019/042388, dated Dec. 10, 2019, 13 pages.

Luria et al., A New Israeli Tobamovirus Isolate Infects Tomato Plants Harboring Tm-22 Resistance Genes. PLOS One, Jan. 20, 2017, 12(1):1-19.

GenBank Acession No. HG975523, Nov. 17, 2015.

*Primary Examiner* — Medina A Ibrahim
(74) *Attorney, Agent, or Firm* — Dentons US LLP; Matthew Madsen

(57) ABSTRACT

Tomato plants exhibiting resistance to *Stemphylium* are provided, together with methods of producing, identifying, or selecting plants or germplasm with a *Stemphylium* resistance phenotype and lacking an undesirable small fruit size trait. Such plants include tomato plants comprising introgressed genomic regions conferring disease resistance. Compositions, including novel polymorphic markers for detecting plants comprising introgressed disease resistance alleles, are further provided.

24 Claims, 1 Drawing Sheet
Specification includes a Sequence Listing.

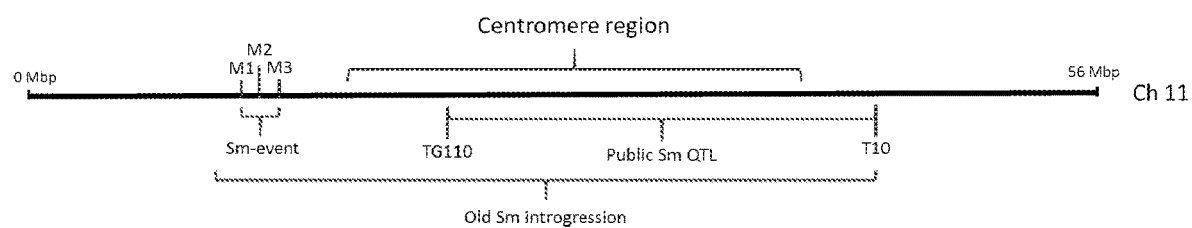

SEQUENCE LISTING

<160> NUMBER OF SEQ ID NOS: 34

<210> SEQ ID NO 1
<211> LENGTH: 1312
<212> TYPE: DNA
<213> ORGANISM: Solanum lycopersicum

<400> SEQUENCE: 1

```
ttctagatgg ttctgttact aaatcacttt caactcactt tgttgattcc tagtctaaaa      60
gaattatcat tgtgaaaaat cagtaggata ttatataacc actcagaatt aacacaatga     120
aaatttgact tgctatgatt tgatgccgta acatcaggta ttctagttat tgtggcctac     180
cattgtttca ttcagttcct tgagcttaca ttgtgacttt ctatattata gagaacattt     240
acagtatact atgtttattt tgggttttcc aaaaatgttg ttttcattta atttaccaag     300
atgttgtttt cttttgtaga ggaatgtgtt ggatgagaaa ataaagcgca aggaagaaca     360
agaggaaatg aaggtacact tttttgtgtc ccattgggta tgaagattac tcaaaacact     420
cttgactacg gatctattaa cacaagattt ggttctgtag gcagaattac aagctatgcg     480
tgaagctgcc cagtggagac gtttgcaagg ttggtccatt ttgctaaamg tgctttatca     540
tacatttatt ctactatctt gctcaaattt tatgtgattg gtacctaatg ttttattcaa     600
ctttgctatt gcttaattgt ctgtgaactc catctatgtt ggttagactc ttgccaaacc     660
catgtcaatc cgacacaatt cgggtgtgga tgtgtgaaga tgcaaataac agaaggaaat     720
caaaaagtag aaatagaata agaacgaaag gaagaaagta atcaacccaa gcaagtatac     780
ttgaacccac taattagcat tcaattacta gaatgaagta gaggaaaaga aatgaactca     840
tatgtctata cttactagaa gaattcgaga gaggttcaat taaactggat tgagaaaatt     900
ccttaaaggg ctctgtcaag ggagctcttc atcaagtaat ttgccttagt atacctttca     960
tgattttata atccccaaag tactcttctc acttaaagcc taactccact ttcttttact    1020
tttttatgcc tcattgcttg gactacacta tggtgcatgt gactagacaa tagaaattct    1080
atttgcagca caaacaataa tcttgtgtag gcgtgtaagg tctgcgtaca ccgactacac    1140
```

| cccaccctgc ccagacccca cttgtaggat cacactgggt atgttgttgt tgtgttgttc | 1200 |
| cgggtatgtg attgtttcct ttgtcatgct ccacacccttt gaaggatata tggttccatc | 1260 |
| tatcgtttgt ggtactagat agtccatttc tgatgaataa aacatacgaa ga | 1312 |

<210> SEQ ID NO 2
<211> LENGTH: 199
<212> TYPE: DNA
<213> ORGANISM: Solanum pimpinellifolium

<400> SEQUENCE: 2

| gagttattct ctcacctgcc ctgaaatgtg tatgtatgaa tacatttagg gatgtcaact | 60 |
| tcaattcata atttcaattc tgaattctcc aaaatttarg atttcaaatt ccaatatttt | 120 |
| ttttcaaata taaaacttga ccaataagat tatattctgc acaattaatg tttatcttat | 180 |
| taactattta tatttatga | 199 |

<210> SEQ ID NO 3
<211> LENGTH: 1968
<212> TYPE: DNA
<213> ORGANISM: Solanum lycopersicum
<220> FEATURE:
<221> NAME/KEY: misc_feature
<222> LOCATION: (466)..(466)
<223> OTHER INFORMATION: n is a, c, g, or t

<400> SEQUENCE: 3

| gagctcctcc tggaggtgca tgcacagtta ttggaagtac ccactcacat ttctctctac | 60 |
| cctctaccaa aagaggatgt tcatatctga tacatcatgc atgaagtatt acagaaacaa | 120 |
| agagggataa attcgtgaat ttagtctatt tgaagaagaa aataccaaat tacgaaggaa | 180 |
| aatctataaa tagaatcaga tagatgaatc aggacatgga gaacaaattg aggggagaaa | 240 |
| agaacaccaa gattacaatt atggtgcatt tgatgagaga ccataaagtt ccttcccta | 300 |
| ccatattttc tttacaattg aatcgatata tctaagtgaa gcaaatcaag gcatgcttc | 360 |
| aaccttccat gattcactag aaataattat gtcaagagag ttccacttta aaatagagat | 420 |
| tggaagttca atcatgacaa atcgcaaggt gtcttctgat tttccngttt gatggaagtg | 480 |
| gtaccaacag caaaaattaa atattgatag cgggagagta tttcctgtta aaggtttcta | 540 |
| gcataagagt catcataaca atgctgagta tcctagttta ttgtgagaag atggagactc | 600 |
| atcgttatca gcttatgatt aggacggtgg ttcatgatgc attgcccaaa taattttaga | 660 |
| aaaagaggca aaagattgtc agtcagagct acttaagttc gaatgaataa gtgatagaat | 720 |
| cttcttctcc atgtgagttt cctagcacat ttgacatcta tttgttccga agggttataa | 780 |
| gtcatgaaga ggtgagcgtt tagcctcttg atgatttacc tggactaaaa tggagatacg | 840 |
| taattaatgg gctgcaattt tattcaacag cttacatatt gttcacggat tcgcaggcat | 900 |
| gaagaattgg aaggttgaag cagaaaaaaa ttgtgcacaa gatccctgtc aaaatttctt | 960 |
| aaagtccctc atatttgatg ggaataaaga agaaccgaag tagatgatga gctgatatac | 1020 |
| ttctaaatcc ttttgatctg atgatctttt tcagctttta agatagtctg caagcgtctt | 1080 |
| ttgtatgata cttttccctg taatgtactt tacccctcccc ttttttgcac cctcttattg | 1140 |
| gaaactccaa atcttcgatc aatgaattat gcagcgacaa aatattcttg ttacatgagc | 1200 |
| aagtacatac cttgacaagt cagcattctt gggagtggta aagaattcaa atcgaagagc | 1260 |
| ccattgtacg gagacatagt gagtggaaaa agacatagga ccatccatcg gaatggaaaa | 1320 |
| aaggaagctt gtctgaatta aatcagcaac cacctcatga tgatcactat gaacctgaat | 1380 |

```
aaatcaaaaa gccttggtga ctaatcacca aatgaagggg ctcaagtgtt tatctcttct    1440
aaataaatcc accaaaacac ttctgtcaaa tgcaaagagt tgtaaagaaa tcatcaacag    1500
gtaaagaata ccttcgtaat agaaggagca tgtctccgtg aaggatgtac atagcgtcgg    1560
ctgatagttt cggtcatctc cagtgtaatt gaaagctaga aggcaacaaa aggatcaata    1620
aactccagaa agcataaact aatgaataaa ccacatgttt aaggcttatt acaagcatga    1680
actttgatgt ataggactac ctcaaggcat cttctagaac cctcttcatg aaaaaaagtc    1740
agggttccac ctatctgttg ccaaagaata aattgaaggt ataagttccc aaccagtcag    1800
gtgcaaatag gcattggtaa tagtactaat gaaaggacca atacactgaa taattcaatt    1860
accatatcac tgaagtaata tgtcgactca gaattttttg gagaaaatct tagaagcact    1920
tggtcatcca gtctaatgtt gtaagatctc cctcgaataa acccttct                1968
```

<210> SEQ ID NO 4
<211> LENGTH: 101
<212> TYPE: DNA
<213> ORGANISM: Solanum pimpinellifolium

<400> SEQUENCE: 4

```
tacgagccgt ctcttgatgc ttttctacca tagattttga tcgtctcgct ktattatact      60
gtttcaccag ttcagcatcc acacttgatc tactcttttc t                         101
```

<210> SEQ ID NO 5
<211> LENGTH: 30
<212> TYPE: DNA
<213> ORGANISM: Artificial sequence
<220> FEATURE:
<223> OTHER INFORMATION: Primer

<400> SEQUENCE: 5

```
gtctcttgat gcttttctac catagatttt                                       30
```

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6

```
gaggctttca atgaggcttc ag                                               22
```

<210> SEQ ID NO 7
<211> LENGTH: 18
<212> TYPE: DNA
<213> ORGANISM: Artificial sequence
<220> FEATURE:
<223> OTHER INFORMATION: Probe

<400> SEQUENCE: 7

```
atcgtctcgc tttattat                                                    18
```

<210> SEQ ID NO 8
<211> LENGTH: 16
<212> TYPE: DNA
<213> ORGANISM: Artificial sequence
<220> FEATURE:
<223> OTHER INFORMATION: Probe

<400> SEQUENCE: 8

```
cgtctcgctg tattat                                                    16

<210> SEQ ID NO 9
<211> LENGTH: 201
<212> TYPE: DNA
<213> ORGANISM: Solanum pimpinellifolium

<400> SEQUENCE: 9
ttgctggaca atacgattta aggatactag acatgtttat gccctctaaa tataatgact    60
gtctaagttg ctctgtcagt aaagcttagt tggacccaaa ytctattctc agtaatgctt   120
agttggaccc aaattctatt ttccttgact tgccatattt ttgggctcgg tcagtggcag   180
atatctcaag gcctctcctt t                                             201

<210> SEQ ID NO 10
<211> LENGTH: 201
<212> TYPE: DNA
<213> ORGANISM: Solanum pimpinellifolium

<400> SEQUENCE: 10
ttgcatatta tgttgttgga cataagacta gtcactacaa aaacatatg aagtcataag     60 ttgctttgaa ttctgctcaa cgttttattt ggttaacgtt wgtcttaatt gttttggtag   120
gttaaatttt ggattctcac tgaagatgtg tgacttatga ataaaagtt gttcagagag    180 tacgttcgta gagtactttt g                                             201

<210> SEQ ID NO 11
<211> LENGTH: 25
<212> TYPE: DNA
<213> ORGANISM: Artificial sequence
<220> FEATURE:
<223> OTHER INFORMATION: Primer

<400> SEQUENCE: 11
tgctttgaat tctgctcaac gtttt                                          25

<210> SEQ ID NO 12
<211> LENGTH: 25
<212> TYPE: DNA
<213> ORGANISM: Artificial sequence
<220> FEATURE:
<223> OTHER INFORMATION: Primer

<400> SEQUENCE: 12
gtcacacatc ttcagtgaga atcca                                          25

<210> SEQ ID NO 13
<211> LENGTH: 22
<212> TYPE: DNA
<213> ORGANISM: Artificial sequence
<220> FEATURE:
<223> OTHER INFORMATION: Probe

<400> SEQUENCE: 13
caaaacaatt aagactaacg tt                                             22

<210> SEQ ID NO 14
<211> LENGTH: 20
<212> TYPE: DNA
<213> ORGANISM: Artificial sequence
<220> FEATURE:
<223> OTHER INFORMATION: Probe

<400> SEQUENCE: 14
```

```
aaacaattaa gacaaacgtt                                                  20

<210> SEQ ID NO 15
<211> LENGTH: 201
<212> TYPE: DNA
<213> ORGANISM: Solanum pimpinellifolium
<220> FEATURE:
<221> NAME/KEY: misc_feature
<222> LOCATION: (61)..(61)
<223> OTHER INFORMATION: n is a, c, g, or t

<400> SEQUENCE: 15
tctcccagtc cattttggaa gaagagtcgc agtgatttgt tcaattatgt tttgaattta     60
ntaaaagtat cttccaatgt tgttttgggt ttcaattgga kttgtgaatt acatgttcat    120
ttattttttt tagaaaggtt tcaagcaaca tgtgcaatga gataattgtt aaataatctt    180
atcagtggat agtttaatta t                                              201

<210> SEQ ID NO 16
<211> LENGTH: 27
<212> TYPE: DNA
<213> ORGANISM: Artificial sequence
<220> FEATURE:
<223> OTHER INFORMATION: Primer

<400> SEQUENCE: 16
gagtcgcagt gatttgttca attatgt                                         27

<210> SEQ ID NO 17
<211> LENGTH: 25
<212> TYPE: DNA
<213> ORGANISM: Artificial sequence
<220> FEATURE:
<223> OTHER INFORMATION: Primer

<400> SEQUENCE: 17
gcacatgttg cttgaaacct ttcta                                           25

<210> SEQ ID NO 18
<211> LENGTH: 17
<212> TYPE: DNA
<213> ORGANISM: Artificial sequence
<220> FEATURE:
<223> OTHER INFORMATION: Probe

<400> SEQUENCE: 18
ttggagttgt gaattac                                                    17

<210> SEQ ID NO 19
<211> LENGTH: 17
<212> TYPE: DNA
<213> ORGANISM: Artificial sequence
<220> FEATURE:
<223> OTHER INFORMATION: Probe

<400> SEQUENCE: 19
ttggatttgt gaattac                                                    17

<210> SEQ ID NO 20
<211> LENGTH: 201
<212> TYPE: DNA
<213> ORGANISM: Solanum pimpinellifolium

<400> SEQUENCE: 20
```

```
aaaacacact gcatgaaagt gttatttaaa gaaatgggag agagtacaag ataagtgaga    60
ctcgaggtct tcaaggcatt gatagattga aaagagaatc wggtcccatt catttgcttt   120
ttaaattgct cagaacagat ttggtcttaa gtttaaagct aatacaggg  agattcggtg   180 aagtagcaac cttttgatga g                                              201

<210> SEQ ID NO 21
<211> LENGTH: 22
<212> TYPE: DNA
<213> ORGANISM: Artificial sequence
<220> FEATURE:
<223> OTHER INFORMATION: Primer

<400> SEQUENCE: 21
gactcgaggt cttcaaggca tt                                             22

<210> SEQ ID NO 22
<211> LENGTH: 27
<212> TYPE: DNA
<213> ORGANISM: Artificial sequence
<220> FEATURE:
<223> OTHER INFORMATION: Primer

<400> SEQUENCE: 22
acttaagacc aaatctgttc tgagcaa                                        27

<210> SEQ ID NO 23
<211> LENGTH: 18
<212> TYPE: DNA
<213> ORGANISM: Artificial sequence
<220> FEATURE:
<223> OTHER INFORMATION: Probe

<400> SEQUENCE: 23
aaaagagaat caggtccc                                                  18

<210> SEQ ID NO 24
<211> LENGTH: 18
<212> TYPE: DNA
<213> ORGANISM: Artificial sequence
<220> FEATURE:
<223> OTHER INFORMATION: Probe

<400> SEQUENCE: 24
aaaagagaat ctggtccc                                                  18

<210> SEQ ID NO 25
<211> LENGTH: 187
<212> TYPE: DNA
<213> ORGANISM: Solanum pimpinellifolium
<220> FEATURE:
<221> NAME/KEY: misc_feature
<222> LOCATION: (58)..(58)
<223> OTHER INFORMATION: n is a, c, g, or t

<400> SEQUENCE: 25
tgatatacat gcttgctagc tggagcttca ctagctctta ttataatgat ggtatcgnca    60
gttgactttc gacgtaatga ccaaatctat gttacattat yggaaaatga cattcattca   120
atcataatat aaaatacaaa atatttaatc atgaagtttt ctagctcgac ataacttagg   180
aattaat                                                             187

<210> SEQ ID NO 26
<211> LENGTH: 25
```

```
<212> TYPE: DNA
<213> ORGANISM: Artificial sequence
<220> FEATURE:
<223> OTHER INFORMATION: Primer

<400> SEQUENCE: 26
agttgacttt cgacgtaatg accaa                                           25

<210> SEQ ID NO 27
<211> LENGTH: 35
<212> TYPE: DNA
<213> ORGANISM: Artificial sequence
<220> FEATURE:
<223> OTHER INFORMATION: Primer

<400> SEQUENCE: 27
gtcgagctag aaaacttcat gattaaatat tttgt                                35

<210> SEQ ID NO 28
<211> LENGTH: 19
<212> TYPE: DNA
<213> ORGANISM: Artificial sequence
<220> FEATURE:
<223> OTHER INFORMATION: Probe

<400> SEQUENCE: 28
atgtcatttt ccaataatg                                                  19

<210> SEQ ID NO 29
<211> LENGTH: 19
<212> TYPE: DNA
<213> ORGANISM: Artificial sequence
<220> FEATURE:
<223> OTHER INFORMATION: Probe

<400> SEQUENCE: 29
atgtcatttt ccgataatg                                                  19

<210> SEQ ID NO 30
<211> LENGTH: 184
<212> TYPE: DNA
<213> ORGANISM: Solanum pimpinellifolium
<220> FEATURE:
<221> NAME/KEY: misc_feature
<222> LOCATION: (138)..(138)
<223> OTHER INFORMATION: n is a, c, g, or t

<400> SEQUENCE: 30
agaaaatcta atcaaatgga atttcttagt tggaattatg actatatttc tacctgcatt      60
tgatgattca tgaaattttc cctaataatg tgtagctact rtccgggagg ataaattacg     120
atcgaaattt caaaaaanta ttttttattt attgcatttt atttattcct aaactatatc    180
cttt                                                                 184

<210> SEQ ID NO 31
<211> LENGTH: 30
<212> TYPE: DNA
<213> ORGANISM: Artificial sequence
<220> FEATURE:
<223> OTHER INFORMATION: Primer

<400> SEQUENCE: 31
acctgcattt gatgattcat gaaattttcc                                      30

<210> SEQ ID NO 32
```

```
<211> LENGTH: 33
<212> TYPE: DNA
<213> ORGANISM: Artificial sequence
<220> FEATURE:
<223> OTHER INFORMATION: Primer

<400> SEQUENCE: 32
aaaggatata gtttaggaat aaataaaatg caa                              33

<210> SEQ ID NO 33
<211> LENGTH: 16
<212> TYPE: DNA
<213> ORGANISM: Artificial sequence
<220> FEATURE:
<223> OTHER INFORMATION: Probe

<400> SEQUENCE: 33
cctcccggat agtagc                                                 16

<210> SEQ ID NO 34
<211> LENGTH: 15
<212> TYPE: DNA
<213> ORGANISM: Artificial sequence
<220> FEATURE:
<223> OTHER INFORMATION: Probe

<400> SEQUENCE: 34
ctcccggaca gtagc                                                  15
```

TOMATO PLANTS WITH IMPROVED DISEASE RESISTANCE

CROSS-REFERENCE TO RELATED APPLICATIONS

This application claims the benefit of priority of U.S. Provisional Application No. 62/701,305, filed Jul. 20, 2018, and U.S. Provisional Application No. 62/815,622, filed Mar. 8, 2019, each of which is herein incorporated by reference in its entirety.

INCORPORATION OF SEQUENCE LISTING

A sequence listing containing the file named "SEMB038US_ST25.txt" which is 12.0 kilobytes (measured in MS-Windows®) and created on Jul. 15, 2019, and comprises 34 sequences, is incorporated herein by reference in its entirety.

FIELD OF THE INVENTION

The present invention relates to the field of plant breeding and more specifically to methods and compositions for producing tomato plants exhibiting improved disease resistance without linked deleterious traits.

BACKGROUND

Disease resistance is an important trait in agriculture, particularly for the production of food crops. Although disease resistance alleles have been identified in tomato, efforts to introduce these alleles into cultivated lines have been hindered by a lack of specific markers linked to the alleles, as well as the presence of deleterious alleles genetically linked to disease resistance alleles that lead to an unacceptable reduction in yield, fruit size, and fruit quality. The use of marker-assisted selection (MAS) in plant breeding has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis, and an often incomplete understanding of the genetic background underlying expression of a desired phenotype. In the absence of accurate and validated markers for use in MAS, it may not be feasible to produce new plant lines exhibiting certain disease resistance phenotypes and acceptable yield, fruit size, and fruit quality.

SUMMARY

In one aspect, the invention provides a *Solanum lycopersicum* plant comprising a recombinant chromosomal segment on chromosome 11, wherein said chromosomal segment comprises a *Stemphylium* resistance allele from *Solanum* pimpinellifolium conferring increased resistance to *Stemphylium* to said plant compared to a plant not comprising said allele, and wherein the chromosomal segment lacks a deleterious allele genetically linked to said *Stemphylium* resistance allele that confers small fruit size when present. In some embodiments, said *Stemphylium* resistance allele is located within a chromosomal segment flanked by marker locus M1 (SEQ ID NO:1) and marker locus M3 (SEQ ID NO:3) on chromosome 11 in said plant. In certain embodiments, said introgressed *Stemphylium* resistance allele is within a chromosomal segment on chromosome 11 comprising a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30). In further embodiments, said plant comprises a *Solanum lycopersicum* allele at marker locus M1 (SEQ ID NO:1) and an *Solanum* pimpinellifolium allele at marker locus M2 (SEQ ID NO:2). In yet further embodiments, said plant further comprises a *Solanum lycopersicum* allele at marker locus M3 (SEQ ID NO:3).

In another aspect, cells, seed, and plant parts comprising a recombinant chromosomal segment on chromosome 11, wherein said chromosomal segment comprises a *Stemphylium* resistance allele from *Solanum pimpinellifolium* conferring increased resistance to *Stemphylium* to said plant compared to a plant not comprising said allele, and wherein the chromosomal segment lacks a deleterious allele genetically linked to said *Stemphylium* resistance allele that confers small fruit size when present are provided. In certain embodiments, a representative sample of seed comprising said chromosomal segment has been deposited under NCMA Accession No. 202103011. Cells, seeds, and plant parts comprising said chromosomal segment are further provided.

In yet another aspect, the invention provides a *Solanum lycopersicum* plant comprising a recombinant chromosomal segment on chromosome 11, wherein said chromosomal segment comprises a *Stemphylium* resistance allele from *Solanum* pimpinellifolium conferring increased resistance to *Stemphylium* to said plant compared to a plant not comprising said allele, and wherein the chromosomal segment lacks a deleterious allele genetically linked to said *Stemphylium* resistance allele that confers small fruit size when present, and wherein said recombinant chromosomal segment further comprises a Tomato Brown Rugose Fruit Virus (TBRFV) resistance allele. In some embodiments, said TBRFV resistance allele is located within a chromosomal segment flanked by marker locus M1 (SEQ ID NO:1) and marker locus M3 (SEQ ID NO:3) on chromosome 11 in said plant. In other embodiments, said plant is homozygous for said TBRFV resistance allele.

In a further aspect, the invention provides a recombinant DNA segment comprising a *Stemphylium* resistance allele from *Solanum* pimpinellifolium that confers to a *Solanum lycopersicum* plant increased resistance to *Stemphylium* and lacking a deleterious allele genetically linked thereto that confers small fruit size. In some embodiments, said recombinant DNA segment comprises a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30). In further embodiments, said recombinant DNA segment is further defined as comprised within a plant, plant part, plant cell, or seed. In yet further embodiments, said DNA segment confers to said plant increased resistance to *Stemphylium*.

In another aspect, methods are provided for producing a plant exhibiting resistance to *Stemphylium*, comprising: a) crossing the plant of claim 1 with itself or with a second tomato plant of a different genotype to produce one or more progeny plants; and b) selecting a progeny plant comprising said *Stemphylium* resistance allele. In some embodiments, selecting said progeny plant comprises detecting a marker locus genetically linked to said *Stemphylium* resistance allele. In other embodiments, selecting said progeny plant comprises detecting a marker locus within or genetically linked to a chromosomal segment flanked in the genome of said plant by marker locus M1 (SEQ ID NO:1) and marker locus M3 (SEQ ID NO:3) on chromosome 11. In further embodiments, selecting a progeny plant comprises detecting at least one polymorphism at a locus selected from the group consisting of marker locus M1 (SEQ ID NO:1), marker locus M2 (SEQ ID NO:2), marker locus M3 (SEQ ID NO:3), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30). In yet further embodiments, selecting a progeny plant comprises detecting: a) a polymorphism at marker locus M1 (SEQ ID NO:1) and a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30); or b) a polymorphism at marker locus M3 (SEQ ID NO:3) and a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30). In certain embodiments, selecting a progeny plant comprises detecting: a) a recurrent parent allele at marker locus M1 (SEQ ID NO:1); and b) a donor allele at a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30). In other embodiments, selecting a progeny plant further comprises detecting a recurrent parent allele at marker M3 (SEQ ID NO:3). In some embodiments, said progeny plant is an $F_2$-$F_6$ progeny plant or producing said progeny plant comprises backcrossing.

In further aspects, methods are provided for producing a tomato plant exhibiting resistance to *Stemphylium*, comprising introgressing into a plant a *Stemphylium* resistance allele from *Solanum pimpinellifolium* within a recombinant chromosomal segment flanked in the genome of said plant by: marker locus M1 (SEQ ID NO:1) and marker locus M3 (SEQ ID NO:3) on chromosome 11; wherein said introgressed *Stemphylium* resistance allele confers to said plant increased resistance to *Stemphylium* compared to a plant not comprising said allele, and wherein said recombinant chromosomal segment lacks a deleterious allele genetically linked to said *Stemphylium* resistance allele that confers a small fruit size trait to said plant when present. In certain embodiments, said introgressed *Stemphylium* resistance allele is within a recombinant chromosomal segment on chromosome 11 comprising a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30). In some embodiments, said recombinant chromosomal segment is defined by: a) a non-introgressed allele at marker locus M1 (SEQ ID NO:1); b) an introgressed allele at a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30); and c) a non-introgressed allele at marker locus M3 (SEQ ID NO:3). Said introgressing may comprise backcrossing, marker-assisted selection, or assaying for *Stemphylium* resistance. Tomato plants obtainable by the methods disclosed herein are further provided.

In yet a further aspect, methods are provided for selecting a tomato plant exhibiting resistance to *Stemphylium*, comprising: a) crossing the tomato plant of claim 1 with itself or with a second tomato plant of a different genotype to produce one or more progeny plants; and b) selecting a progeny plant comprising said *Stemphylium* resistance allele. In certain embodiments, selecting said progeny plant comprises detecting a marker locus genetically linked to said *Stemphylium* resistance allele. In some embodiments, selecting said progeny plant comprises detecting a marker locus within or genetically linked to a chromosomal segment flanked in the genome of said plant marker locus M1 (SEQ ID NO:1) and marker locus M3 (SEQ ID NO:3) on chromosome 11. In further embodiments, selecting a progeny plant comprises detecting at least one polymorphism at a locus selected from the group consisting of marker locus M1 (SEQ ID NO:1), marker locus M2 (SEQ ID NO:2), marker locus M3 (SEQ ID NO:3), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30). In yet further embodiments, said progeny plant is an $F_2$-$F_6$ progeny plant, or producing said progeny plant comprises backcrossing.

BRIEF DESCRIPTION OF THE DRAWINGS

FIG. 1: Shows a schematic overview of different *Stemphylium* introgressions on the physical map of chromosome 11.

DETAILED DESCRIPTION

Gray leaf spot disease in tomato occurs worldwide and is caused by four fungal species of *Stemphylium: S. solani, S. floridanum, S botyosum*, and *S. vesicarum*. These fungi cause gray lesions on the foliage of plants and, in cases of severe disease pressure, complete defoliation. Gray leaf spot disease can be managed through application of fungicides or the use of *Stemphylium* resistant tomato cultivars. *Stemphylium* resistance is conferred by the Sm gene, which originates from wild tomato accession *Solanum pimpinellifolium* PI 79532 and confers resistance to all four *Stemphylium* species that cause gray leaf spot disease. The Sm gene was found to be located between markers T10 (isozyme marker) and TG110 (RFLP marker) on tomato chromosome 11 and found to act in an incompletely dominant manner. However, PCR-based high-throughput makers that could be used for marker-assisted breeding have not been reported.

To date the *Stemphylium* resistance conferred by the Sm gene has been associated with commercially unacceptable reductions in yield and small fruit size. This has hampered the ability to use the resistance in a commercially relevant manner. The current inventors were surprisingly able to remove the deleterious yield and small fruit size phenotype from the *Stemphylium* resistance conferred by the Sm gene, allowing it to be used in a commercial setting. This was surprisingly possible despite the Sm gene being closely associated with the centromeric region of chromosome 11, which has a very low rate of recombination. Despite this, the current inventors were able to generate very small reduced recombinant segments with a centromeric region that originates from *S. lycopersicum* rather than *S. pimpinellifolium*, and lacking associated deleterious traits.

The present inventors also found that the Sm locus is located outside the region flanked by markers T10 and TG110, based on the physical map of tomato chromosome 11 (FIG. 1). TG110 was found to be located at 20.4 Mbp of tomato chromosome 11 of the public tomato genome map version SL2.50 (The Tomato Genome Consortium; *Nature* 485:635-641, 2012; publically available on the internet through solgenomics.net). T10, whose sequence was found as Genbank accession number X14041.1, was found to be located at 52.1 Mbp of tomato chromosome 11 of the public tomato genome map version SL2.50. The present inventors surprisingly found that the Sm locus is located between 8.9 and 9.8 Mbp of tomato chromosome 11 and were able to identify novel genetic markers for identifying and tracking Sm during plant breeding and allowing removal of genomic regions that confer undesirable traits, such as small fruit size. Having discovered that the *Stemphylium* resistance alleles and the small fruit size alleles can be removed using the novel markers provided herein, the inventors created for the first time a recombinant event that can be used by breeders to readily transfer the *Stemphylium* resistance alleles without the reduced yield and small fruit size trait to other tomato plants.

The present inventors have discovered for the first time that M1, a SNP marker with a [C/A] change at 8,894,829 bp on chromosome 11 of the public tomato genome map version SL2.50, M2, a SNP marker with a [G/A] change at 9,591,834 bp of chromosome 11 of the public tomato genome map version SL2.50, and M3, a SNP marker with a [T/A] change at 9,826,973 bp of chromosome 11 of the public tomato genome map version SL2.50 can be used to identify this region, wherein M1 and M3 are flanking markers. The public genome of tomato is available at for example www.solgenomics.net, and one skilled in the art would understand that the marker sequences provided for the first time in the instant application could be located on any version (or later version) of the public genome. One aspect of the invention therefore provides plants comprising *Solanum lycopersicum* DNA at marker locus M1 (SEQ ID NO:1), and introgressed donor DNA at marker locus M2 (SEQ ID NO:2). In further embodiments, the invention provides plants comprising *Solanum lycopersicum* parent DNA at marker locus M3 (SEQ ID NO:3), and introgressed donor DNA at marker locus M2 (SEQ ID NO:2).

In certain embodiments, tomato plants are provided comprising an introgressed allele on chromosome 11, wherein said introgressed allele confers to said plant increased resistance to *Stemphylium* compared to a plant not comprising said allele. In further embodiments, said plant lacks a further allele, genetically linked to said introgressed allele, that confers small fruit size when present.

Further provided herein are reduced recombinant introgressions comprising a genomic interval between marker locus M1 (SEQ ID NO:1) and marker locus M3 (SEQ ID NO:3) on chromosome 11, wherein said reduced genomic interval lacks deleterious small fruit size alleles associated with larger *Stemphylium* resistance introgressions.

In other embodiments, the invention provides plants comprising one or more of the novel recombinant introgressions provided herein. These novel introgressions provide robust resistance to *Stemphylium*, while avoiding the reduction in performance characteristics associated with conventional introgressions of the Sm gene. Methods of producing the plants described herein are further provided. In certain embodiments, the invention provides tomato line FDR-I15-0403V comprising an exemplary reduced introgression described herein, a sample of the seed of which has been deposited under NCMA Accession No. 202103011.

The invention further provides novel trait-linked markers which can be used to produce plants comprising novel recombinant introgressions on chromosome 11 conferring *Stemphylium* resistance as described herein. In particular embodiments, the invention provides the markers shown in Table 1.

Methods of producing plants comprising the reduced recombinant introgressions described herein are further provided. In some examples, donor DNA from a resistant donor parent is introgressed into a cultivated plant line (the recurrent parent line). M1 (SEQ ID NO:1) is used to select the allele of the recurrent parent, and M2 (SEQ ID NO:2) is used to select the allele of the resistance donor parent resulting in a reduced genomic interval lacking deleterious traits associated with larger *Stemphylium* resistance introgressions. In further embodiments, M3 (SEQ ID NO:3) is further used to select the allele of the recurrent parent resulting in a further reduced genomic interval conferring *Stemphylium* resistance.

In certain embodiments, the invention provides methods of producing or selecting a tomato plant exhibiting resistance to *Stemphylium* comprising: a) crossing a tomato plant provided herein with itself or with a second tomato plant of a different genotype to produce one or more progeny plants; and b) selecting a progeny plant comprising said first introgressed allele or said second introgressed allele. In some embodiments, methods of the invention comprise selecting a progeny plant by detecting at least one polymorphism at a locus selected from the group consisting of marker locus M1 (SEQ ID NO:1), M2 (SEQ ID NO:2), and M3 (SEQ ID NO:3).

Because genetically diverse plant lines can be difficult to cross, the introgression of *Stemphylium* resistance alleles into cultivated lines using conventional breeding methods could require prohibitively large segregating populations for progeny screens with an uncertain outcome. Marker-assisted selection (MAS) is therefore essential for the effective introgression of *Stemphylium* resistance alleles into elite cultivars. However, previously known markers for *Stemphylium* resistance have failed to discriminate between donor DNA conferring disease resistance and donor DNA conferring deleterious traits. This has been further complicated by the previous inability to resolve the specific regions associated with disease resistance. For the first time, the present invention enables effective MAS by providing improved and validated markers for detecting genotypes associated with disease resistance without the need to grow large populations of plants to maturity in order to observe the phenotype.

Further provided herein is use of the genetic region on chromosome 11 that confers resistance to *Stemphylium*, wherein the region also confers resistance against leaf and fruit symptoms caused by the Tomato Brown Rugose Fruit Virus (TBRFV). Tomato Brown Rugose Fruit Virus is a rapidly spreading tobamovirus that causes spots to form on the leaves of tomato plants and developing fruit. The brown and black necrotic spots on the fruit render the fruit unmarketable. This virus was originally discovered in 2016 in Jordan but has been reported to have spread to important tomato growing regions, such as Israel, Turkey, the Netherlands, Mexico, and western USA.

In certain embodiments, SNP markers M1, M2, and M3, which are described above, can also be used to select for the TBRFV resistance trait. Additional markers that can be used to select for the TBRFV resistance trait are M4, a SNP marker with a [T/G] change at 8,891,489 bp on chromosome 11 of the public tomato genome map version SL2.50; M5, a SNP marker with a [C/T] change at 9,355,794 bp on chromosome 11 of the public tomato genome map version SL2.50; M6, a SNP marker with a [A/T] change at 9,401,319 bp on chromosome 11 of the public tomato genome map version SL2.50; M7, a SNP marker with a [G/T] change at 9,406,414 bp on chromosome 11 of the public tomato genome map version SL2.50; M8, a SNP marker with a [A/T] change at 9,421,426 bp on chromosome 11 of the public tomato genome map version SL2.50; M9, a SNP marker with a [T/C] change at 9,470,789 bp on chromosome 11 of the public tomato genome map version SL2.50; and M10, a SNP marker with a [A/G] change at 9,756,371 bp on chromosome 11 of the public tomato genome map version SL2.50. Markers M4, M5, M6, M7, M8, M9, and M10 can also be used to select for the *Stemphylium* resistance allele described herein.

In certain embodiments markers M1 and M3 are used to select the allele of the recurrent parent line and any of markers M2, M4, M5, M6, M7, M8, M9, or M10 is used to select for the donor parent line.

I. Genomic Regions, Alleles, and Polymorphisms Associated with *Stemphylium* Resistance in Tomato Plants The invention provides novel introgressions of one or more alleles associated with *Stemphylium* disease resistance without the detrimental small fruit size trait in tomato plants, together with polymorphic nucleic acids and linked markers for tracking the introgressions during plant breeding.

Tomato lines exhibiting *Stemphylium* resistance are known in the art and may be used together with the novel trait-linked markers provided herein in accordance with certain embodiments of the invention. For example, the wild tomato accession *Solanum pimpinellifolium* PI 79532, which also carries the designation LA2348, can be used as a source for *Stemphylium* resistance. This line is available at the U.S. National Plant Germplasm System and the Tomato Genetic Resource Center in Davis, Calif., USA. Using the improved genetic markers and assays of the invention, the present inventors were able to successfully identify novel reduced introgressions from *S. pimpinellifolium* that confer *Stemphylium* resistance to the plant with fewer deleterious traits when introgressed into a cultivated line. In certain embodiments, the invention provides tomato plants comprising donor DNA between marker loci M1 (SEQ ID NO:1) and M3 (SEQ ID NO:3) on chromosome 11.

The novel introgressions provided herein confer robust resistance to *Stemphylium*, while avoiding the reduction in yield and small fruit size seen with conventional introgressions. The invention therefore represents a significant advance in the art.

II. Introgression of Genomic Regions Associated with *Stemphylium* Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a *Stemphylium* resistant plant into a cultivated line. The invention further provides markers for identifying and tracking the novel introgressions disclosed herein during plant breeding, including the markers set forth in Table 1.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistant phenotype.

Tomato plants comprising one or more introgressed regions associated with a desired phenotype wherein at least 10%, 25%, 50%, 75%, 90%, or 99% of the remaining genomic sequences carry markers characteristic of the recurrent parent germplasm are also provided. Tomato plants comprising an introgressed region comprising regions closely linked to or adjacent to the genomic regions and markers provided herein and associated with a disease resistance phenotype are also provided.

III. Development of Disease Resistant Tomato Varieties

For most breeding objectives, commercial breeders work with germplasm that is "cultivated," "cultivated type," or "elite." These cultivated lines may be used as recurrent parents or as a source of recurrent parent alleles during breeding. Cultivated or elite germplasm is easier to breed because it generally performs well when evaluated for horticultural performance. Many cultivated tomato types have been developed and are known in the art as being agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. Non-cultivated germplasm may be used as a source of donor alleles during breeding. However, this approach generally presents significant difficulties due to fertility problems associated with crosses between diverse lines, and genetically linked deleterious alleles from the non-cultivated parent. For example, non-cultivated tomato types can provide alleles associated with disease resistance. However, these non-cultivated types may have poor horticultural qualities such as poor quality, poor architecture, low yield, or small fruit size.

The process of introgressing desirable resistance genes from non-cultivated lines into elite cultivated lines while avoiding problems with genetically linked deleterious alleles or low heritability is a long and often arduous process. In deploying alleles derived from wild relatives it is often desirable to introduce a minimal or truncated introgression that provides the desired trait but lacks detrimental effects. To aid introgression reliable marker assays are preferable to phenotypic screens. Success is furthered by simplifying genetics for key attributes to allow focus on genetic gain for quantitative traits such as disease resistance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, the inventors' discovery of accurate markers associated with disease resistance will facilitate the development of tomato plants having beneficial phenotypes. For example, seed can be genotyped using the markers of the present invention to select for plants comprising desired genomic regions associated with disease resistance. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the M1a and M1g genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the removal of deleterious genomic fragments, and pyramiding traits that are genetically tightly linked. Therefore suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among tomato species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Marker Assisted Breeding and Genetic Engineering Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita, et al. (1989) *Genomics*, 8(2), 271-278), denaturing gradient gel electrophoresis (Myers (1985) EPO 0273085), or cleavage fragment length polymorphisms (Life Technologies, Inc., Gaithersburg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques*, 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a tomato plant a genotype associated with disease resistance, identify a tomato plant with a genotype associated with disease resistance, and to select a tomato plant with a genotype associated with disease resistance. In certain embodiments of methods of the invention, polymorphic nucleic acids can be used to produce a tomato plant that comprises in its genome an introgressed locus associated with disease resistance. In certain embodiments of the invention, polymorphic nucleic acids can be used to breed progeny tomato plants comprising a locus or loci associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to a condition where the two alleles at a locus are different.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in tomato plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. (1986) Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to detect polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is described in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Some embodiments include methods for treating tomato, tomato plant parts, or the soil or substrate in which tomato plants are grown or intended to be grown with an active compound or a combination of active compounds. In some embodiments, the tomato plants are suspected of being or becoming infected with a disease, or the methods are for protecting or treating plants from fungal and bacterial infections. In some embodiments the disease is a fungal infection, and the embodiments include methods for protecting from a fungal disease. In further embodiments, the tomato plant comprises a recombinant chromosomal segment on chromosome 11 that comprises a *Stemphylium* resistance allele. In some embodiments, said chromosomal segment lacks a deleterious allele that confers a small fruit size trait to said plant when present. In further embodiments, the treatment increases tomato yield. In some embodiments, the active compound or combination of active compounds comprises a fungicidal active ingredient. In certain embodiments, the active compound is selected from the following groups: (1) inhibitors of the ergosterol synthesis, (2) inhibitors of the respiratory chain at complex I or II, (3) inhibitors of the respiratory chain at complex III, (4) inhibitors of the mitosis and cell division, (5) compounds capable of having a multisite action, (6) compounds capable of inducing a host defense, (7) inhibitors of the amino acid and/or protein biosynthesis, (8) inhibitors of the ATP production, (9) inhibitors of the cell wall synthesis, (10) inhibitors of the lipid and membrane synthesis, (11) inhibitors of the melanine biosynthesis, (12) inhibitors of the nucleic acid synthesis, (13) inhibitors of the signal transduction, (14) compounds capable of acting as uncoupler, and (15) other fungicides. Examples of such active compounds, their synthesis, and analysis are provided in European Patent Application EP3335559A1.

In some embodiments, inhibitors of the ergosterol synthesis are selected from the group consisting of (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)-cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (5)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Mefentrifluconazole, and (1.082) Ipfentrifluconazole.

In some embodiments, inhibitors of the respiratory chain at complex I or II are selected from the group consisting of (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR, 9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3 S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, and (2.056) N-cyclopropyl-N-(2-cyclopropylbenzyl)-3-(difluoromethyl)-5-fluoro-1-methyl-1H-pyrazole-4-carboxamide.

In some embodiments, inhibitors of the respiratory chain at complex III are selected from the group consisting of (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, and (3.029) methyl {5-[3-(2,4-dimethylphenyl)-1H-pyrazol-1-yl]-2-methylbenzyl}carbamate.

In some embodiments, inhibitors of the mitosis and cell division are selected from the group consisting of (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019)

4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, and (4.025) N-(4-chloro-2,6-difluorophenyl)-4-(2-chloro-4-fluorophenyl)-1,3-dimethyl-1H-pyrazol-5-amine.

In some embodiments, compounds capable of having a multisite action are selected from the group consisting of (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, and (5.023) 6-ethyl-5,7-dioxo-6,7-dihydro-5H-pyrrolo[3',4':5,6][1,4]dithiino[2,3-c][1,2]thiazole-3-carbonitrile.

In some embodiments, compounds capable of inducing a host defense are selected from the group consisting of (6.001) acibenzolar-S-methyl, (6.002) isotianil, (6.003) probenazole, and (6.004) tiadinil.

In some embodiments, inhibitors of the amino acid and/or protein biosynthesis are selected from the group consisting of (7.001) cyprodinil, (7.002) kasugamycin, (7.003) kasugamycin hydrochloride hydrate, (7.004) oxytetracycline, (7.005) pyrimethanil, and (7.006) 3-(5-fluoro-3,3,4,4-tetramethyl-3,4-dihydroisoquinolin-1-yl)quinolone.

In some embodiments, inhibitor of the ATP production is selected from the group consisting of (8.001) silthiofam.

In some embodiments, inhibitors of the cell wall synthesis are selected from the group consisting of (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, and (9.009) (2Z)-3-(4-tert-butylphenyl)-3-(2-chloropyridin-4-yl)-1-(morpholin-4-yl)prop-2-en-1-one.

In some embodiments, inhibitors of the lipid and membrane synthesis are selected from the group consisting of (10.001) propamocarb, (10.002) propamocarb hydrochloride, and (10.003) tolclofos-methyl.

In some embodiments, inhibitors of the melanine biosynthesis are selected from the group consisting of (11.001) tricyclazole, and (11.002) 2,2,2-trifluoroethyl {3-methyl-1-[(4-methylbenzoyl)amino]butan-2-yl}carbamate.

In some embodiments, inhibitors of the nucleic acid synthesis are selected from the group consisting of (12.001) benalaxyl, (12.002) benalaxyl-M (kiralaxyl), (12.003) metalaxyl, and (12.004) metalaxyl-M (mefenoxam).

In some embodiments, inhibitors of the signal transduction are selected from the group consisting of (13.001) fludioxonil, (13.002) iprodione, (13.003) procymidone, (13.004) proquinazid, (13.005) quinoxyfen, and (13.006) vinclozolin.

In some embodiments, compounds capable of acting as uncoupler are selected from the group consisting of (14.001) fluazinam, and (14.002) meptyldinocap.

In some embodiments, other fungicides are selected from the group consisting of (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-[5-[2-chloro-6-(prop-2-yn-1-yloxy)phenyl]-4,5-dihydro-1,2-oxazol-3-yl]-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, and (15.062)

5-fluoro-4-imino-3-methyl-1-[(4-methylphenyl)sulfonyl]-3,4-dihydropyrimidin-2(1H)-one.

In certain embodiments, the active compound or combination of active compounds is selected from:

(1.001) cyproconazole, (1.002) difenoconazole, (1.003) epoxiconazole, (1.004) fenhexamid, (1.010) imazalil, (1.012) ipconazole, (1.013) metconazole, (1.017) propiconazole, (1.018) prothioconazole, (1.020) spiroxamine, (1.021) tebuconazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.059) 5-(4-chlorobenzyl)-2-(chloromethyl)-2-methyl-1-(1H-1,2,4-triazol-1-ylmethyl)cyclopentanol, (1.081) Mefentrifluconazole, and (1.082) Ipfentrifluconazole, (2.001) benzovindiflupyr, (2.002) bixafen, (2.003) boscalid, (2.005) fluopyram, (2.007) fluxapyroxad, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.021) sedaxane, (2.027) 3-(difluoromethyl)-1-methyl-N-(1,1,3-trimethyl-2,3-dihydro-1H-inden-4-yl)-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (3.003) azoxystrobin, (3.007) dimoxystrobin, (3.012) fluoxastrobin, (3.013) kresoxim-methyl, (3.016) picoxystrobin, (3.017) pyraclostrobin, (3.020) trifloxystrobin, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (4.005) pencycuron, (4.007) thiophanate-methyl, (4.012) 4-(2-bromo-4-fluorophenyl)-N-(2,6-difluorophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine, (5.003) captan, (5.004) chlorothalonil, (5.011) dodine, (5.012) folpet, (5.013) mancozeb, (5.015) metiram, (5.018) propineb, (6.002) isotianil, (7.001) cyprodinil, (7.005) pyrimethanil, (12.003) metalaxyl, (12.004) metalaxyl-M (mefenoxam), (13.001) fludioxonil, (13.002) iprodione, (13.004) proquinazid, (13.005) quinoxyfen, (14.001) fluazinam, (14.002) meptyldinocap, (15.008) cyflufenamid, (15.010) cyprosulfamide, (15.011) flutianil, (15.012) fosetyl-aluminium, (15.016) metrafenone, (15.027) pyriofenone (chlazafenone), and (15.047) 3-(4,4-difluoro-3,3-dimethyl-3,4-dihydroisoquinolin-1-yl)quinolone, (15.048) 4-amino-5-fluoropyrimidin-2-ol (tautomeric form: 4-amino-5-fluoropyrimidin-2(1H)-one), (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.062) 5-fluoro-4-imino-3-methyl-1-[(4-methylphenyl)sulfonyl]-3,4-dihydropyrimidin-2(1H)-one.

In certain embodiments, the active compound or combination of active compounds is selected from:

(1.002) difenoconazole, (1.010) imazalil, (1.012) ipconazole, (1.018) prothioconazole, (1.020) spiroxamine, (1.021) tebuconazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.059) 5-(4-chlorobenzyl)-2-(chloromethyl)-2-methyl-1-(1H-1,2,4-triazol-1-ylmethyl)cyclopentanol, (1.081) Mefentrifluconazole, and (1.082) Ipfentrifluconazole, (2.001) benzovindiflupyr, (2.002) bixafen, (2.005) fluopyram, (2.007) fluxapyroxad, (2.017) penflufen, (2.018) penthiopyrad, (2.019) pydiflumetofen, (2.021) sedaxane, (2.027) 3-(difluoromethyl)-1-methyl-N-(1,1,3-trimethyl-2,3-dihydro-1H-inden-4-yl)-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (3.003) azoxystrobin, (3.012) fluoxastrobin, (3.016) picoxystrobin, (3.017) pyraclostrobin, (3.020) trifloxystrobin, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (4.005) pencycuron, (4.007) thiophanate-methyl, (4.012) 4-(2-bromo-4-fluorophenyl)-N-(2,6-difluorophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine, (5.004) chlorothalonil, (5.011) dodine, (5.012) folpet, (5.013) mancozeb, (5.018) propineb, (6.002) isotianil, (7.005) pyrimethanil, (12.003) metalaxyl, (12.004) metalaxyl-M (mefenoxam), (13.001) fludioxonil, (13.004) proquinazid, (14.001) fluazinam, (14.002) meptyldinocap, (15.008) cyflufenamid, (15.027) pyriofenone (chlazafenone), (15.047) 3-(4,4-difluoro-3,3-dimethyl-3,4-dihydroisoquinolin-1-yl)quinolone, (15.048) 4-amino-5-fluoropyrimidin-2-ol (tautomeric form: 4-amino-5-fluoropyrimidin-2(1H)-one), (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.062) 5-fluoro-4-imino-3-methyl-1-[(4-methylphenyl)sulfonyl]-3,4-dihydropyrimidin-2(1H)-one.

In certain embodiments, the active compound or combination of active compounds is selected from:

(1.012) ipconazole, (1.018) prothioconazole, (1.020) spiroxamine, (1.021) tebuconazole, (2.002) bixafen, (2.005) fluopyram, (2.017) penflufen, (2.027) 3-(difluoromethyl)-1-methyl-N-(1,1,3-trimethyl-2,3-dihydro-1H-inden-4-yl)-1H-pyrazole-4-carboxamide, (2.038) N-(5-chloro-2-isopropylbenzyl)-N- cyclopropyl-3-(difluoromethyl)-5-fluoro-1-methyl-1H-pyrazole-4-carboxamide,
(3.020) trifloxystrobin, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate,
(4.005) pencycuron,
(5.004) chlorothalonil, (5.013) mancozeb, (5.018) propineb,
(12.003) metalaxyl, (12.004) metalaxyl-M (mefenoxam),
(13.001) fludioxonil, (13.004) proquinazid,
(15.008) cyflufenamid, and (15.047) 3-(4,4-difluoro-3,3-dimethyl-3,4-dihydroisoquinolin-1-yl)quinoline.

In certain embodiments, the active compound or combination of active compounds are selected from the group (G1) consisting of the following mixtures: (I.01)+(1.001), (I.01)+(1.002), (I.01)+(1.003), (I.01)+(1.004), (I.01)+(1.005), (I.01)+(1.006), (I.01)+(1.007), (I.01)+(1.008), (I.01)+(1.009), (I.01)+(1.010), (I.01)+(1.011), (I.01)+(1.012), (I.01)+(1.013), (I.01)+(1.014), (I.01)+(1.015), (I.01)+(1.016), (I.01)+(1.017), (I.01)+(1.018), (I.01)+(1.019), (I.01)+(1.020), (I.01)+(1.021), (I.01)+(1.022), (I.01)+(1.023), (I.01)+(1.024), (I.01)+(1.025), (I.01)+(1.026), (I.01)+(1.027), (I.01)+(1.028), (I.01)+(1.029), (I.01)+(1.030), (I.01)+(1.031), (I.01)+(1.032), (I.01)+(1.033), (I.01)+(1.034), (I.01)+(1.035), (I.01)+(1.036), (I.01)+(1.037), (I.01)+(1.038), (I.01)+(1.039), (I.01)+(1.040), (I.01)+(1.041), (I.01)+(1.042), (I.01)+(1.043), (I.01)+(1.044), (I.01)+(1.045), (I.01)+(1.046), (I.01)+(1.047), (I.01)+(1.048), (I.01)+(1.049), (I.01)+(1.050), (I.01)+(1.051), (I.01)+(1.052), (I.01)+(1.053), (I.01)+(1.054), (I.01)+(1.055), (I.01)+(1.056), (I.01)+(1.057), (I.01)+(1.058), (I.01)+(1.059), (I.01)+(1.060), (I.01)+(1.061), (I.01)+(1.062), (I.01)+(1.063), (I.01)+(1.064), (I.01)+(1.065), (I.01)+(1.066), (I.01)+(1.067), (I.01)+(1.068), (I.01)+(1.069), (I.01)+(1.070), (I.01)+(1.071), (I.01)+(1.072), (I.01)+(1.073), (I.01)+(1.074), (I.01)+(1.075), (I.01)+(1.076), (I.01)+(1.077), (I.01)+(1.078), (I.01)+(1.079), (I.01)+(1.080), (I.01)+(1.081), (I.01)+(1.082), (I.01)+(2.001), (I.01)+(2.002), (I.01)+(2.003), (I.01)+(2.004), (I.01)+(2.005), (I.01)+(2.006), (I.01)+(2.007), (I.01)+(2.008), (I.01)+(2.009), (I.01)+(2.010), (I.01)+(2.011), (I.01)+(2.012), (I.01)+(2.013), (I.01)+(2.014), (I.01)+(2.015), (I.01)+(2.016), (I.01)+(2.017), (I.01)+(2.018), (I.01)+(2.019), (I.01)+(2.020), (I.01)+(2.021), (I.01)+(2.022), (I.01)+(2.023), (I.01)+(2.024), (I.01)+(2.025), (I.01)+(2.026), (I.01)+(2.027), (I.01)+(2.028), (I.01)+(2.029), (I.01)+(2.030), (I.01)+(2.031), (I.01)+(2.032), (I.01)+(2.033), (I.01)+(2.034), (I.01)+(2.035), (I.01)+(2.036), (I.01)+(2.037), (I.01)+(2.038), (I.01)+(2.039), (I.01)+(2.040), (I.01)+(2.041), (I.01)+(2.042), (I.01)+(2.043), (I.01)+(2.044), (I.01)+(2.045), (I.01)+(2.046), (I.01)+(2.047), (I.01)+(2.048), (I.01)+(2.049), (I.01)+(2.050), (I.01)+(2.051), (I.01)+(2.052), (I.01)+(2.053), (I.01)+(2.054), (I.01)+(2.055), (I.01)+(2.056), (I.01)+(3.001), (I.01)+(3.002), (I.01)+(3.003), (I.01)+(3.004), (I.01)+(3.005), (I.01)+(3.006), (I.01)+(3.007), (I.01)+(3.008), (I.01)+(3.009), (I.01)+(3.010), (I.01)+(3.011), (I.01)+(3.012), (I.01)+(3.013), (I.01)+(3.014), (I.01)+(3.015), (I.01)+(3.016), (I.01)+(3.017), (I.01)+(3.018), (I.01)+(3.019), (I.01)+(3.020), (I.01)+(3.021), (I.01)+(3.022), (I.01)+(3.023), (I.01)+(3.024), (I.01)+(3.025), (I.01)+(3.026), (I.01)+(3.027), (I.01)+(3.028), (I.01)+(3.029), (I.01)+(4.001), (I.01)+(4.002), (I.01)+(4.003), (I.01)+(4.004), (I.01)+(4.005), (I.01)+(4.006), (I.01)+(4.007), (I.01)+(4.008), (I.01)+(4.009), (I.01)+(4.010), (I.01)+(4.011), (I.01)+(4.012), (I.01)+(4.013), (I.01)+(4.014), (I.01)+(4.015), (I.01)+(4.016), (I.01)+(4.017), (I.01)+(4.018), (I.01)+(4.019), (I.01)+(4.020), (I.01)+(4.021), (I.01)+(4.022), (I.01)+(4.023), (I.01)+(4.024), (I.01)+(4.025), (I.01)+(5.001), (I.01)+(5.002), (I.01)+(5.003), (I.01)+(5.004), (I.01)+(5.005), (I.01)+(5.006), (I.01)+(5.007), (I.01)+(5.008), (I.01)+(5.009), (I.01)+(5.010), (I.01)+(5.011), (I.01)+(5.012), (I.01)+(5.013), (I.01)+(5.014), (I.01)+(5.015), (I.01)+(5.016), (I.01)+(5.017), (I.01)+(5.018), (I.01)+(5.019), (I.01)+(5.020), (I.01)+(5.021), (I.01)+(5.022), (I.01)+(5.023), (I.01)+(6.001), (I.01)+(6.002), (I.01)+(6.003), (I.01)+(6.004), (I.01)+(7.001), (I.01)+(7.002), (I.01)+(7.003), (I.01)+(7.004), (I.01)+(7.005), (I.01)+(7.006), (I.01)+(8.001), (I.01)+(9.001), (I.01)+(9.002), (I.01)+(9.003), (I.01)+(9.004), (I.01)+(9.005), (I.01)+(9.006), (I.01)+(9.007), (I.01)+(9.008), (I.01)+(9.009), (I.01)+(10.001), (I.01)+(10.002), (I.01)+(10.003), (I.01)+(11.001), (I.01)+(11.002), (I.01)+(12.001), (I.01)+(12.002), (I.01)+(12.003), (I.01)+(12.004), (I.01)+(13.001), (I.01)+(13.002), (I.01)+(13.003), (I.01)+(13.004), (I.01)+(13.005), (I.01)+(13.006), (I.01)+(14.001), (I.01)+(14.002), (I.01)+(15.001), (I.01)+(15.002), (I.01)+(15.003), (I.01)+(15.004), (I.01)+(15.005), (I.01)+(15.006), (I.01)+(15.007), (I.01)+(15.008), (I.01)+(15.009), (I.01)+(15.010), (I.01)+(15.011), (I.01)+(15.012), (I.01)+(15.013), (I.01)+(15.014), (I.01)+(15.015), (I.01)+(15.016), (I.01)+(15.017), (I.01)+(15.018), (I.01)+(15.019), (I.01)+(15.020), (I.01)+(15.021), (I.01)+(15.022), (I.01)+(15.023), (I.01)+(15.024), (I.01)+(15.025), (I.01)+(15.026), (I.01)+(15.027), (I.01)+(15.028), (I.01)+(15.029), (I.01)+(15.030), (I.01)+(15.031), (I.01)+(15.032), (I.01)+(15.033), (I.01)+(15.034), (I.01)+(15.035), (I.01)+(15.036), (I.01)+(15.037), (I.01)+(15.038), (I.01)+(15.039), (I.01)+(15.040), (I.01)+(15.041), (I.01)+(15.042), (I.01)+(15.043), (I.01)+(15.044), (I.01)+(15.045), (I.01)+(15.046), (I.01)+(15.047), (I.01)+(15.048), (I.01)+(15.049), (I.01)+(15.050), (I.01)+(15.051), (I.01)+(15.052), (I.01)+(15.053), (I.01)+(15.054), (I.01)+(15.055), (I.01)+(15.056), (I.01)+(15.057), (I.01)+(15.058), (I.01)+(15.059), (I.01)+(15.060), (I.01)+(15.061), and (I.01)+(15.062).

In certain embodiments, the active compound or combination of active compounds are selected from the group (G2) consisting of the following mixtures: (I.59)+(1.001), (I.59)+(1.002), (I.59)+(1.003), (I.59)+(1.004), (I.59)+(1.005), (I.59)+(1.006), (I.59)+(1.007), (I.59)+(1.008), (I.59)+(1.009), (I.59)+(1.010), (I.59)+(1.011), (I.59)+(1.012), (I.59)+(1.013), (I.59)+(1.014), (I.59)+(1.015), (I.59)+(1.016), (I.59)+(1.017), (I.59)+(1.018), (I.59)+(1.019), (I.59)+(1.020), (I.59)+(1.021), (I.59)+(1.022), (I.59)+(1.023), (I.59)+(1.024), (I.59)+(1.025), (I.59)+(1.026), (I.59)+(1.027), (I.59)+(1.028), (I.59)+(1.029), (I.59)+(1.030), (I.59)+(1.031), (I.59)+(1.032), (I.59)+(1.033), (I.59)+(1.034), (I.59)+(1.035), (I.59)+(1.036), (I.59)+(1.037), (I.59)+(1.038), (I.59)+(1.039), (I.59)+(1.040), (I.59)+(1.041), (I.59)+(1.042), (I.59)+(1.043), (I.59)+(1.044), (I.59)+(1.045), (I.59)+(1.046), (I.59)+(1.047), (I.59)+(1.048), (I.59)+(1.049), (I.59)+(1.050), (I.59)+(1.051), (I.59)+(1.052), (I.59)+(1.053), (I.59)+(1.054), (I.59)+(1.055), (I.59)+(1.056), (I.59)+(1.057), (I.59)+(1.058), (I.59)+(1.059), (I.59)+(1.060), (I.59)+(1.061), (I.59)+(1.062), (I.59)+(1.063), (I.59)+(1.064), (I.59)+(1.065), (I.59)+(1.066), (I.59)+(1.067), (I.59)+(1.068), (I.59)+(1.069), (I.59)+(1.070), (I.59)+(1.071), (I.59)+(1.072), (I.59)+(1.073), (I.59)+(1.074), (I.59)+(1.075), (I.59)+(1.076), (I.59)+(1.077), (I.59)+(1.078), (I.59)+(1.079), (I.59)+(1.080), (I.59)+(1.081), (I.59)+(1.082), (I.59)+(2.001), (I.59)+(2.002), (I.59)+(2.003), (I.59)+(2.004), (I.59)+(2.005), (I.59)+(2.006), (I.59)+(2.007), (I.59)+(2.008), (I.59)+(2.009), (I.59)+(2.010), (I.59)+(2.011), (I.59)+(2.012), (I.59)+(2.013), (I.59)+(2.014), (I.59)+(2.015), (I.59)+(2.016), (I.59)+(2.017), (I.59)+(2.018), (I.59)+(2.019), (I.59)+(2.020), (I.59)+(2.021), (I.59)+(2.022), (I.59)+(2.023), (I.59)+(2.024), (I.59)+(2.025), (I.59)+(2.026), (I.59)+(2.027), (I.59)+(2.028), (I.59)+(2.029), (I.59)+(2.030), (I.59)+(2.031), (I.59)+(2.032), (I.59)+(2.033), (I.59)+(2.034), (I.59)+(2.035), (I.59)+(2.036), (I.59)+(2.037), (I.59)+(2.038), (I.59)+(2.039), (I.59)+(2.040), (I.59)+(2.041), (I.59)+(2.042), (I.59)+(2.043), (I.59)+(2.044), (I.59)+(2.045), (I.59)+(2.046), (I.59)+(2.047), (I.59)+(2.048), (I.59)+(2.049), (I.59)+(2.050), (I.59)+(2.051), (I.59)+(2.052), (I.59)+(2.053), (I.59)+(2.054), (I.59)+(2.055), (I.59)+(2.056), (I.59)+(3.001), (I.59)+(3.002), (I.59)+(3.003), (I.59)+(3.004), (I.59)+(3.005), (I.59)+(3.006), (I.59)+(3.007), (I.59)+(3.008), (I.59)+(3.009), (I.59)+(3.010), (I.59)+(3.011), (I.59)+(3.012), (I.59)+(3.013), (I.59)+(3.014), (I.59)+(3.015), (I.59)+(3.016), (I.59)+(3.017), (I.59)+(3.018), (I.59)+(3.019), (I.59)+(3.020), (I.59)+(3.021), (I.59)+(3.022), (I.59)+(3.023), (I.59)+(3.024), (I.59)+(3.025), (I.59)+(3.026), (I.59)+(3.027), (I.59)+(3.028), (I.59)+(3.029), (I.59)+(4.001), (I.59)+(4.002), (I.59)+(4.003), (I.59)+(4.004), (I.59)+(4.005), (I.59)+(4.006), (I.59)+(4.007), (I.59)+(4.008), (I.59)+(4.009), (I.59)+(4.010), (I.59)+(4.011), (I.59)+(4.012), (I.59)+(4.013), (I.59)+(4.014), (I.59)+(4.015), (I.59)+(4.016), (I.59)+(4.017), (I.59)+(4.018), (I.59)+(4.019), (I.59)+(4.020), (I.59)+(4.021), (I.59)+(4.022), (I.59)+(4.023), (I.59)+(4.024), (I.59)+(4.025), (I.59)+(5.001), (I.59)+(5.002), (I.59)+(5.003), (I.59)+(5.004), (I.59)+(5.005), (I.59)+(5.006), (I.59)+(5.007), (I.59)+(5.008), (I.59)+(5.009), (I.59)+(5.010), (I.59)+(5.011), (I.59)+(5.012), (I.59)+(5.013), (I.59)+(5.014), (I.59)+(5.015), (I.59)+(5.016), (I.59)+(5.017), (I.59)+(5.018), (I.59)+(5.019), (I.59)+(5.020), (I.59)+(5.021), (I.59)+(5.022), (I.59)+(5.023), (I.59)+(6.001), (I.59)+(6.002), (I.59)+(6.003), (I.59)+(6.004), (I.59)+(7.001), (I.59)+(7.002), (I.59)+(7.003), (I.59)+(7.004), (I.59)+(7.005), (I.59)+(7.006), (I.59)+(8.001), (I.59)+(9.001), (I.59)+(9.002), (I.59)+(9.003), (I.59)+(9.004), (I.59)+(9.005), (I.59)+(9.006), (I.59)+(9.007), (I.59)+(9.008), (I.59)+(9.009), (I.59)+(10.001), (I.59)+(10.002), (I.59)+(10.003), (I.59)+(11.001), (I.59)+(11.002), (I.59)+(12.001), (I.59)+(12.002), (I.59)+(12.003), (I.59)+(12.004), (I.59)+(13.001), (I.59)+(13.002), (I.59)+(13.003), (I.59)+(13.004), (I.59)+(13.005), (I.59)+(13.006), (I.59)+(14.001), (I.59)+(14.002), (I.59)+(15.001), (I.59)+(15.002), (I.59)+(15.003), (I.59)+(15.004), (I.59)+(15.005), (I.59)+(15.006), (I.59)+(15.007), (I.59)+(15.008), (I.59)+(15.009), (I.59)+(15.010), (I.59)+(15.011), (I.59)+(15.012), (I.59)+(15.013), (I.59)+(15.014), (I.59)+(15.015), (I.59)+(15.016), (I.59)+(15.017), (I.59)+(15.018), (I.59)+(15.019), (I.59)+(15.020), (I.59)+(15.021), (I.59)+(15.022), (I.59)+(15.023), (I.59)+(15.024), (I.59)+(15.025), (I.59)+(15.026), (I.59)+(15.027), (I.59)+(15.028), (I.59)+(15.029), (I.59)+(15.030), (I.59)+(15.031), (I.59)+(15.032), (I.59)+(15.033), (I.59)+(15.034), (I.59)+(15.035), (I.59)+(15.036), (I.59)+(15.037), (I.59)+(15.038), (I.59)+(15.039), (I.59)+(15.040), (I.59)+(15.041), (I.59)+(15.042), (I.59)+(15.043), (I.59)+(15.044), (I.59)+(15.045), (I.59)+(15.046), (I.59)+(15.047), (I.59)+(15.048), (I.59)+(15.049), (I.59)+(15.050), (I.59)+(15.051), (I.59)+(15.052), (I.59)+(15.053), (I.59)+(15.054), (I.59)+(15.055), (I.59)+(15.056), (I.59)+(15.057), (I.59)+(15.058), (I.59)+(15.059), (I.59)+(15.060), (I.59)+(15.061), and (I.59)+(15.062).

In certain embodiments, the active compound or combination of active compounds are selected from the group (G3) consisting of the following mixtures: (I.81)+(1.001), (I.81)+(1.002), (I.81)+(1.003), (I.81)+(1.004), (I.81)+(1.005), (I.81)+(1.006), (I.81)+(1.007), (I.81)+(1.008), (I.81)+(1.009), (I.81)+(1.010), (I.81)+(1.011), (I.81)+(1.012), (I.81)+(1.013), (I.81)+(1.014), (I.81)+(1.015), (I.81)+(1.016), (I.81)+(1.017), (I.81)+(1.018), (I.81)+(1.019), (I.81)+(1.020), (I.81)+(1.021), (I.81)+(1.022), (I.81)+(1.023), (I.81)+(1.024), (I.81)+(1.025), (I.81)+(1.026), (I.81)+(1.027), (I.81)+(1.028), (I.81)+(1.029), (I.81)+(1.030), (I.81)+(1.031), (I.81)+(1.032), (I.81)+(1.033), (I.81)+(1.034), (I.81)+(1.035), (I.81)+(1.036), (I.81)+(1.037), (I.81)+(1.038), (I.81)+(1.039), (I.81)+(1.040), (I.81)+(1.041), (I.81)+(1.042), (I.81)+(1.043), (I.81)+(1.044), (I.81)+(1.045), (I.81)+(1.046), (I.81)+(1.047), (I.81)+(1.048), (I.81)+(1.049), (I.81)+(1.050), (I.81)+(1.051), (I.81)+(1.052), (I.81)+(1.053), (I.81)+(1.054), (I.81)+(1.055), (I.81)+(1.056), (I.81)+(1.057), (I.81)+(1.058), (I.81)+(1.059), (I.81)+(1.060), (I.81)+(1.061), (I.81)+(1.062), (I.81)+(1.063), (I.81)+(1.064), (I.81)+(1.065), (I.81)+(1.066), (I.81)+(1.067), (I.81)+(1.068), (I.81)+(1.069), (I.81)+(1.070), (I.81)+(1.071), (I.81)+(1.072), (I.81)+(1.073), (I.81)+(1.074), (I.81)+(1.075), (I.81)+(1.076), (I.81)+(1.077), (I.81)+(1.078), (I.81)+(1.079), (I.81)+(1.080), (I.81)+(1.081), (I.81)+(1.082), (I.81)+(2.001), (I.81)+(2.002), (I.81)+(2.003), (I.81)+(2.004), (I.81)+(2.005), (I.81)+(2.006), (I.81)+(2.007), (I.81)+(2.008), (I.81)+(2.009), (I.81)+(2.010), (I.81)+(2.011), (I.81)+(2.012), (I.81)+(2.013), (I.81)+(2.014), (I.81)+(2.015), (I.81)+(2.016), (I.81)+(2.017), (I.81)+(2.018), (I.81)+(2.019), (I.81)+(2.020), (I.81)+(2.021), (I.81)+(2.022), (I.81)+(2.023), (I.81)+(2.024), (I.81)+(2.025), (I.81)+(2.026), (I.81)+(2.027), (I.81)+(2.028), (I.81)+(2.029), (I.81)+(2.030), (I.81)+(2.031), (I.81)+(2.032), (I.81)+(2.033), (I.81)+(2.034), (I.81)+(2.035), (I.81)+(2.036), (I.81)+(2.037), (I.81)+(2.038), (I.81)+(2.039), (I.81)+(2.040), (I.81)+(2.041), (I.81)+(2.042), (I.81)+(2.043), (I.81)+(2.044), (I.81)+(2.045), (I.81)+(2.046), (I.81)+(2.047), (I.81)+(2.048), (I.81)+(2.049), (I.81)+(2.050), (I.81)+(2.051), (I.81)+(2.052), (I.81)+(2.053), (I.81)+(2.054), (I.81)+(2.055), (I.81)+(2.056), (I.81)+(3.001), (I.81)+(3.002), (I.81)+(3.003), (I.81)+(3.004), (I.81)+(3.005), (I.81)+(3.006), (I.81)+(3.007), (I.81)+(3.008), (I.81)+(3.009), (I.81)+(3.010), (I.81)+(3.011), (I.81)+(3.012), (I.81)+(3.013), (I.81)+(3.014), (I.81)+(3.015), (I.81)+(3.016), (I.81)+(3.017), (I.81)+(3.018), (I.81)+(3.019), (I.81)+(3.020), (I.81)+(3.021), (I.81)+(3.022), (I.81)+(3.023), (I.81)+(3.024), (I.81)+(3.025), (I.81)+(3.026), (I.81)+(3.027), (I.81)+(3.028), (I.81)+(3.029), (I.81)+(4.001), (I.81)+(4.002), (I.81)+(4.003), (I.81)+(4.004), (I.81)+(4.005), (I.81)+(4.006), (I.81)+(4.007), (I.81)+(4.008), (I.81)+(4.009), (I.81)+(4.010), (I.81)+(4.011), (I.81)+(4.012), (I.81)+(4.013), (I.81)+(4.014), (I.81)+(4.015), (I.81)+(4.016), (I.81)+(4.017), (I.81)+(4.018), (I.81)+(4.019), (I.81)+(4.020), (I.81)+(4.021), (I.81)+(4.022), (I.81)+(4.023), (I.81)+(4.024), (I.81)+(4.025), (I.81)+(5.001), (I.81)+(5.002), (I.81)+(5.003), (I.81)+(5.004), (I.81)+(5.005), (I.81)+(5.006), (I.81)+(5.007), (I.81)+(5.008), (I.81)+(5.009), (I.81)+(5.010), (I.81)+(5.011), (I.81)+(5.012), (I.81)+(5.013), (I.81)+(5.014), (I.81)+(5.015), (I.81)+(5.016), (I.81)+(5.017), (I.81)+(5.018), (I.81)+(5.019), (I.81)+(5.020), (I.81)+(5.021), (I.81)+(5.022), (I.81)+(5.023), (I.81)+(6.001), (I.81)+(6.002), (I.81)+(6.003), (I.81)+(6.004), (I.81)+(7.001), (I.81)+(7.002), (I.81)+(7.003), (I.81)+(7.004), (I.81)+(7.005), (I.81)+(7.006), (I.81)+(8.001), (I.81)+(9.001), (I.81)+(9.002), (I.81)+(9.003), (I.81)+(9.004), (I.81)+(9.005), (I.81)+(9.006), (I.81)+

(9.007), (I.81)+(9.008), (I.81)+(9.009), (I.81)+(10.001), (I.81)+(10.002), (I.81)+(10.003), (I.81)+(11.001), (I.81)+(11.002), (I.81)+(12.001), (I.81)+(12.002), (I.81)+(12.003), (I.81)+(12.004), (I.81)+(13.001), (I.81)+(13.002), (I.81)+(13.003), (I.81)+(13.004), (I.81)+(13.005), (I.81)+(13.006), (I.81)+(14.001), (I.81)+(14.002), (I.81)+(15.001), (I.81)+(15.002), (I.81)+(15.003), (I.81)+(15.004), (I.81)+(15.005), (I.81)+(15.006), (I.81)+(15.007), (I.81)+(15.008), (I.81)+(15.009), (I.81)+(15.010), (I.81)+(15.011), (I.81)+(15.012), (I.81)+(15.013), (I.81)+(15.014), (I.81)+(15.015), (I.81)+(15.016), (I.81)+(15.017), (I.81)+(15.018), (I.81)+(15.019), (I.81)+(15.020), (I.81)+(15.021), (I.81)+(15.022), (I.81)+(15.023), (I.81)+(15.024), (I.81)+(15.025), (I.81)+(15.026), (I.81)+(15.027), (I.81)+(15.028), (I.81)+(15.029), (I.81)+(15.030), (I.81)+(15.031), (I.81)+(15.032), (I.81)+(15.033), (I.81)+(15.034), (I.81)+(15.035), (I.81)+(15.036), (I.81)+(15.037), (I.81)+(15.038), (I.81)+(15.039), (I.81)+(15.040), (I.81)+(15.041), (I.81)+(15.042), (I.81)+(15.043), (I.81)+(15.044), (I.81)+(15.045), (I.81)+(15.046), (I.81)+(15.047), (I.81)+(15.048), (I.81)+(15.049), (I.81)+(15.050), (I.81)+(15.051), (I.81)+(15.052), (I.81)+(15.053), (I.81)+(15.054), (I.81)+(15.055), (I.81)+(15.056), (I.81)+(15.057), (I.81)+(15.058), (I.81)+(15.059), (I.81)+(15.060), (I.81)+(15.061), and (I.81)+(15.062).

In certain embodiments, the active compound or combination of active compounds are selected from the group (G4) consisting of the following mixtures: (I.91)+(1.001), (I.91)+(1.002), (I.91)+(1.003), (I.91)+(1.004), (I.91)+(1.005), (I.91)+(1.006), (I.91)+(1.007), (I.91)+(1.008), (I.91)+(1.009), (I.91)+(1.010), (I.91)+(1.011), (I.91)+(1.012), (I.91)+(1.013), (I.91)+(1.014), (I.91)+(1.015), (I.91)+(1.016), (I.91)+(1.017), (I.91)+(1.018), (I.91)+(1.019), (I.91)+(1.020), (I.91)+(1.021), (I.91)+(1.022), (I.91)+(1.023), (I.91)+(1.024), (I.91)+(1.025), (I.91)+(1.026), (I.91)+(1.027), (I.91)+(1.028), (I.91)+(1.029), (I.91)+(1.030), (I.91)+(1.031), (I.91)+(1.032), (I.91)+(1.033), (I.91)+(1.034), (I.91)+(1.035), (I.91)+(1.036), (I.91)+(1.037), (I.91)+(1.038), (I.91)+(1.039), (I.91)+(1.040), (I.91)+(1.041), (I.91)+(1.042), (I.91)+(1.043), (I.91)+(1.044), (I.91)+(1.045), (I.91)+(1.046), (I.91)+(1.047), (I.91)+(1.048), (I.91)+(1.049), (I.91)+(1.050), (I.91)+(1.051), (I.91)+(1.052), (I.91)+(1.053), (I.91)+(1.054), (I.91)+(1.055), (I.91)+(1.056), (I.91)+(1.057), (I.91)+(1.058), (I.91)+(1.059), (I.91)+(1.060), (I.91)+(1.061), (I.91)+(1.062), (I.91)+(1.063), (I.91)+(1.064), (I.91)+(1.065), (I.91)+(1.066), (I.91)+(1.067), (I.91)+(1.068), (I.91)+(1.069), (I.91)+(1.070), (I.91)+(1.071), (I.91)+(1.072), (I.91)+(1.073), (I.91)+(1.074), (I.91)+(1.075), (I.91)+(1.076), (I.91)+(1.077), (I.91)+(1.078), (I.91)+(1.079), (I.91)+(1.080), (I.91)+(1.081), (I.91)+(1.082), (I.91)+(2.001), (I.91)+(2.002), (I.91)+(2.003), (I.91)+(2.004), (I.91)+(2.005), (I.91)+(2.006), (I.91)+(2.007), (I.91)+(2.008), (I.91)+(2.009), (I.91)+(2.010), (I.91)+(2.011), (I.91)+(2.012), (I.91)+(2.013), (I.91)+(2.014), (I.91)+(2.015), (I.91)+(2.016), (I.91)+(2.017), (I.91)+(2.018), (I.91)+(2.019), (I.91)+(2.020), (I.91)+(2.021), (I.91)+(2.022), (I.91)+(2.023), (I.91)+(2.024), (I.91)+(2.025), (I.91)+(2.026), (I.91)+(2.027), (I.91)+(2.028), (I.91)+(2.029), (I.91)+(2.030), (I.91)+(2.031), (I.91)+(2.032), (I.91)+(2.033), (I.91)+(2.034), (I.91)+(2.035), (I.91)+(2.036), (I.91)+(2.037), (I.91)+(2.038), (I.91)+(2.039), (I.91)+(2.040), (I.91)+(2.041), (I.91)+(2.042), (I.91)+(2.043), (I.91)+(2.044), (I.91)+(2.045), (I.91)+(2.046), (I.91)+(2.047), (I.91)+(2.048), (I.91)+(2.049), (I.91)+(2.050), (I.91)+(2.051), (I.91)+(2.052), (I.91)+(2.053), (I.91)+(2.054), (I.91)+(2.055), (I.91)+(2.056), (I.91)+(3.001), (I.91)+(3.002), (I.91)+(3.003), (I.91)+(3.004), (I.91)+(3.005), (I.91)+(3.006), (I.91)+(3.007), (I.91)+(3.008), (I.91)+(3.009), (I.91)+(3.010), (I.91)+(3.011), (I.91)+(3.012), (I.91)+(3.013), (I.91)+(3.014), (I.91)+(3.015), (I.91)+(3.016), (I.91)+(3.017), (I.91)+(3.018), (I.91)+(3.019), (I.91)+(3.020), (I.91)+(3.021), (I.91)+(3.022), (I.91)+(3.023), (I.91)+(3.024), (I.91)+(3.025), (I.91)+(3.026), (I.91)+(3.027), (I.91)+(3.028), (I.91)+(3.029), (I.91)+(4.001), (I.91)+(4.002), (I.91)+(4.003), (I.91)+(4.004), (I.91)+(4.005), (I.91)+(4.006), (I.91)+(4.007), (I.91)+(4.008), (I.91)+(4.009), (I.91)+(4.010), (I.91)+(4.011), (I.91)+(4.012), (I.91)+(4.013), (I.91)+(4.014), (I.91)+(4.015), (I.91)+(4.016), (I.91)+(4.017), (I.91)+(4.018), (I.91)+(4.019), (I.91)+(4.020), (I.91)+(4.021), (I.91)+(4.022), (I.91)+(4.023), (I.91)+(4.024), (I.91)+(4.025), (I.91)+(5.001), (I.91)+(5.002), (I.91)+(5.003), (I.91)+(5.004), (I.91)+(5.005), (I.91)+(5.006), (I.91)+(5.007), (I.91)+(5.008), (I.91)+(5.009), (I.91)+(5.010), (I.91)+(5.011), (I.91)+(5.012), (I.91)+(5.013), (I.91)+(5.014), (I.91)+(5.015), (I.91)+(5.016), (I.91)+(5.017), (I.91)+(5.018), (I.91)+(5.019), (I.91)+(5.020), (I.91)+(5.021), (I.91)+(5.022), (I.91)+(5.023), (I.91)+(6.001), (I.91)+(6.002), (I.91)+(6.003), (I.91)+(6.004), (I.91)+(7.001), (I.91)+(7.002), (I.91)+(7.003), (I.91)+(7.004), (I.91)+(7.005), (I.91)+(7.006), (I.91)+(8.001), (I.91)+(9.001), (I.91)+(9.002), (I.91)+(9.003), (I.91)+(9.004), (I.91)+(9.005), (I.91)+(9.006), (I.91)+(9.007), (I.91)+(9.008), (I.91)+(9.009), (I.91)+(10.001), (I.91)+(10.002), (I.91)+(10.003), (I.91)+(11.001), (I.91)+(11.002), (I.91)+(12.001), (I.91)+(12.002), (I.91)+(12.003), (I.91)+(12.004), (I.91)+(13.001), (I.91)+(13.002), (I.91)+(13.003), (I.91)+(13.004), (I.91)+(13.005), (I.91)+(13.006), (I.91)+(14.001), (I.91)+(14.002), (I.91)+(15.001), (I.91)+(15.002), (I.91)+(15.003), (I.91)+(15.004), (I.91)+(15.005), (I.91)+(15.006), (I.91)+(15.007), (I.91)+(15.008), (I.91)+(15.009), (I.91)+(15.010), (I.91)+(15.011), (I.91)+(15.012), (I.91)+(15.013), (I.91)+(15.014), (I.91)+(15.015), (I.91)+(15.016), (I.91)+(15.017), (I.91)+(15.018), (I.91)+(15.019), (I.91)+(15.020), (I.91)+(15.021), (I.91)+(15.022), (I.91)+(15.023), (I.91)+(15.024), (I.91)+(15.025), (I.91)+(15.026), (I.91)+(15.027), (I.91)+(15.028), (I.91)+(15.029), (I.91)+(15.030), (I.91)+(15.031), (I.91)+(15.032), (I.91)+(15.033), (I.91)+(15.034), (I.91)+(15.035), (I.91)+(15.036), (I.91)+(15.037), (I.91)+(15.038), (I.91)+(15.039), (I.91)+(15.040), (I.91)+(15.041), (I.91)+(15.042), (I.91)+(15.043), (I.91)+(15.044), (I.91)+(15.045), (I.91)+(15.046), (I.91)+(15.047), (I.91)+(15.048), (I.91)+(15.049), (I.91)+(15.050), (I.91)+(15.051), (I.91)+(15.052), (I.91)+(15.053), (I.91)+(15.054), (I.91)+(15.055), (I.91)+(15.056), (I.91)+(15.057), (I.91)+(15.058), (I.91)+(15.059), (I.91)+(15.060), (I.91)+(15.061), and (I.91)+(15.062).

In certain embodiments, the active compound or combination of active compounds are selected from the mixtures belonging to group (G1) or (G2).

In certain embodiments, the active compound or combination of active compounds are selected from the group (G1-A) consisting of the following mixtures: (I.01)+(1.012), (I.01)+(1.018), (I.01)+(1.020), (I.01)+(1.021), (I.01)+(2.002), (I.01)+(2.005), (I.01)+(2.017), (I.01)+(2.027), (I.01)+(2.038), (I.01)+(3.020), (I.01)+(3.025), (I.01)+(4.005), (I.01)+(5.004), (I.01)+(5.013), (I.01)+(5.018), (I.01)+(12.003), (I.01)+(12.004), (I.01)+(13.001), (I.01)+(13.004), (I.01)+(15.008), (I.01)+(15.047).

In certain embodiments, the active compound or combination of active compounds are selected from the group (G2-A) consisting of the following mixtures: (I.59)+(1.012), (I.59)+(1.018), (I.59)+(1.020), (I.59)+(1.021), (I.59)+(2.002), (I.59)+(2.005), (I.59)+(2.017), (I.59)+(2.027), (I.59)+(2.038), (I.59)+(3.020), (I.59)+(3.025), (I.59)+ (4.005), (I.59)+(5.004), (I.59)+(5.013), (I.59)+(5.018), (I.59)+(12.003), (I.59)+(12.004), (I.59)+(13.001), (I.59)+ (13.004), (I.59)+(15.008), (I.59)+(15.047).

In certain embodiments, the active compound or combination of active compounds are selected from the group (G3-A) consisting of the following mixtures: (I.81)+(1.012), (I.81)+(1.018), (I.81)+(1.020), (I.81)+(1.021), (I.81)+ (2.002), (I.81)+(2.005), (I.81)+(2.017), (I.81)+(2.027), (I.81)+(2.038), (I.81)+(3.020), (I.81)+(3.025), (I.81)+ (4.005), (I.81)+(5.004), (I.81)+(5.013), (I.81)+(5.018), (I.81)+(12.003), (I.81)+(12.004), (I.81)+(13.001), (I.81)+ (13.004), (I.81)+(15.008), (I.81)+(15.047).

In certain embodiments, the active compound or combination of active compounds are selected from the group (G4-A) consisting of the following mixtures: (I.91)+(1.012), (I.91)+(1.018), (I.91)+(1.020), (I.91)+(1.021), (I.91)+ (2.002), (I.91)+(2.005), (I.91)+(2.017), (I.91)+(2.027), (I.91)+(2.038), (I.91)+(3.020), (I.91)+(3.025), (I.91)+ (4.005), (I.91)+(5.004), (I.91)+(5.013), (I.91)+(5.018), (I.91)+(12.003), (I.91)+(12.004), (I.91)+(13.001), (I.91)+ (13.004), (I.91)+(15.008), (I.91)+(15.047).

In certain embodiments, the active compound or combination of active compounds are selected from the mixtures belonging to group (G1-A) or (G2-A).

In certain embodiments, the active compound or combination of active compounds can be present in a broad range of effective weight ratio of A:B, for example in a range of 100:1 to 1:100, preferably in a weight ratio of 50:1 to 1:50, most preferably in a weight ratio of 20:1 to 1:20. Further ratios of A:B which can be used according to the present invention with increasing preference in the order given are: 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

Where a compound (A) or a compound (B) can be present in isomeric forms and/or tautomeric forms, such a compound is understood hereinabove and hereinbelow also to include, where applicable, corresponding isomeric and/or tautomeric forms or mixtures thereof, even when these are not specifically mentioned in each case.

Various genetic engineering technologies have been developed and may be used by those of skill in the art to introduce traits in plants. In certain aspects of the claimed invention, traits are introduced into tomato plants via altering or introducing a single genetic locus or transgene into the genome of a variety or progenitor thereof. Methods of genetic engineering to modify, delete, or insert genes and polynucleotides into the genomic DNA of plants are well-known in the art.

In specific embodiments of the invention, improved tomato lines can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a tomato plant genome (see, for example Sauer et al., *Plant Physiol,* 170(4):1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the invention or may, alternatively, be used for the preparation of transgenes which can be introduced by backcrossing. Methods for the transformation of plants that are well-known to those of skill in the art and applicable to many crop species include, but are not limited to, electroporation, microprojectile bombardment, *Agrobacterium*-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Nat. Biotechnol.*, 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Nat. Biotechnol.*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, for example, Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13:344-348, 1994), and Ellul et al. (*Theor. Appl. Genet.*, 107:462-469, 2003).

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which tomato plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of tomato breeding. An "elite population" is an assortment of elite individuals or varieties that can be used to represent the state of the art in terms of agronomically superior genotypes of a given crop species, such as tomato. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein, "tolerance locus" means a locus associated with tolerance or resistance to disease. For instance, a tolerance locus according to the present invention may, in one embodiment, control tolerance or susceptibility to *Stemphylium*.

As used herein, "tolerance" or "improved tolerance" in a plant refers to the ability of the plant to perform well, for example by maintaining yield, under disease conditions. Tolerance may also refer to the ability of a plant to maintain a plant vigor phenotype under disease conditions. Tolerance is a relative term, indicating that a "tolerant" plant is more able to maintain performance compared to a different (less tolerant) plant (e.g. a different plant variety) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance of different plants, plant varieties, or plant families under disease conditions, and furthermore, will also recognize the phenotypic gradations of "tolerance."

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

As used herein, "resistance allele" means the nucleic acid sequence associated with tolerance or resistance to disease.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. Deposit Information

A deposit was made of at least 625 seeds of tomato line FDR-I15-0403V, which comprises the reduced introgression described herein. The deposit was made with the Provasoli-Guillard National Center for Marine Algae and Microbiota (NCMA), Bigelow Laboratory for Ocean Science, 60 Bigelow Drive, East Boothbay, Me. 04544. The deposit is assigned NCMA Accession No. 202103011, and the date of deposit was Mar. 11, 2021. Access to the deposit will be available during the pendency of the application to persons entitled thereto upon request. The deposit has been accepted under the Budapest Treaty and will be maintained in the NCMA Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

Example 1. Mapping of the *Stemphylium* Resistance Locus

Two mapping populations were developed from an internal donor line containing the *Stemphylium* resistance locus derived from line PI 79532. In the $F_2$ generation of the mapping populations segregating for the *Stemphylium* resistance locus, it was determined that the resistance is most likely to be completely dominant with a 3:1 segregation ratio. In a preliminary mapping study, it was determined that the *Stemphylium* resistance locus was located within a 16 cM region on chromosome 11. The interstitial markers within this region were tested for accuracy across a broad germplasm panel but were not found to be fully predictive of disease resistance in all tested lines. When the tomato genome sequence became available, we learned that this 16 cM region spanned the centromere and was equivalent to ~38.8 Mbp of genomic sequence and this precluded our ability to accurately discern the actual position of the QTL in a biparental population. Accordingly, a modified association mapping approach was taken to identify more predictive markers across the diversity of the germplasm. In this approach, inbred lines that were phenotypically confirmed for *Stemphylium* resistance were cross-referenced with lines that were fingerprinted. 147 internal inbred lines were found to have a known *Stemphylium* resistance phenotype and that were fingerprinted. The lines were subsequently sorted in two phenotypic groups: resistant or susceptible. To ease the marker analysis, markers monomorphic between the two phenotypic groups were discarded and lines for which >20% missing data were removed from the analysis. For all the remaining markers, a Chi-square test statistic was calculated and used to determine if a marker was significantly associated with the disease phenotype (i.e., whether resistant class predominately had one homozygous genotype and the susceptible class had the other homozygous genotype for biallelic SNP assay). Using this approach, marker M1, a SNP marker with a [C/A] change at 8,894,829 bp on chromosome 11 of the public tomato genome map version SL2.50, was found as significantly associated with *Stemphylium* resistance.

Additional markers that are associated with *Stemphylium* resistance were identified using a modified association mapping approach. A 50 Mbp region on chromosome 11 was sequence captured and resultant SNPs were cataloged. To identify potentially causative SNPs, pairwise comparisons were made between SNPs detected in resistant and susceptible lines. Of all loci that were polymorphic between resistant and susceptible genotypes in these comparisons, only 76 tightly clustered SNPs on chromosome 11 were useful for consistently discriminating resistant and susceptible individuals in response to *Stemphylium*. This collection of loci encompasses 1.8 cM on chromosome 11 and corresponds to the interval of 8,894,829 to 9,826,973 bp of the public tomato genome map version SL2.50. This region confers *S. pimpinellifolium*-derived resistance to *Stemphylium* and contains markers M1, M2, a SNP marker with a [G/A] change at 9,591,834 bp of chromosome 11 of the public tomato genome map version SL2.50, and M3, a SNP marker with a [T/A] change at 9,826,973 bp of chromosome 11 of the public tomato genome map version SL2.50.

TABLE 1

Markers for identifying and tracking the *Stemphylium* resistance locus.

| Marker Name | Marker Sequence (SEQ ID NO.) | Genetic Map Position (cM) | Public Chr. | Public Position of SNP SL2.50 (bp) | Marker Size (bp) | SNP Position in Marker (bp) | SNP Change |
|---|---|---|---|---|---|---|---|
| M1 | 1 | 34.35 | 11 | 8,894,829 | 1213 | 529 | [C/A] |
| M2 | 2 | 35.7 | 11 | 9,591,834 | 199 | 99 | [G/A] |
| M3 | 3 | 36.15 | 11 | 9,826,973 | 1968 | 787 | [T/A] |

Example 2. Breeding Event Creation

To aid breeding efforts, a breeding event donor was developed for the *Stemphylium* resistance allele without the detrimental small fruit size allele that could be used across different breeding programs. The mean fruit weight for each of the lines from the $BC_3F_3$ population was compared to the fruit weights of the *Stemphylium* resistance donor line and the recurrent parent lines. As shown in Table 2, the line "$BC_3F_3$ Line 2" had mean fruit weight similar to that of the recurrent parent lines. Genetic analysis showed that this line also contained the smallest introgression and was subsequently used to develop the *Stemphylium* resistance event donor. A single $BC_3F_5$ line was selected as the event donor and finished as tomato line FDR-I15-0403V, and a sample of seed of this line has been deposited under NCMA Accession No. 202103011. The event was found to be 0.5 cM in size, while the distance between flanking markers, M1 and M3, is 1.8 cM. Markers M1, M2, and M3 can be used to select for the reduced introgression conferring *Stemphylium* resistance. When introgressing the breeding event, especially when replacing an existing *Stemphylium* introgression, it is important to use marker M2 to track the resistance locus, which comprises an allele from *S. pimpinellifolium*, while the flanking markers M1 and M3 are used to track the recurrent parent allele.

TABLE 2

Comparison of mean fruit weights of $BC_3F_3$ introgression lines, the original *Stemphylium* resistance donor line, and the recurrent parent lines.

| Pedigree | Mean Fruit Weight (kg) |
| --- | --- |
| $BC_3F_3$ Line 1 | 0.15 |
| $BC_3F_3$ Line 2 | 0.20 |
| $BC_3F_3$ Line 3 | 0.16 |
| $BC_3F_3$ Line 4 | 0.17 |
| $BC_3F_3$ Line 5 | 0.16 |
| $BC_3F_3$ Line 6 | 0.18 |
| $BC_3F_3$ Line 7 | 0.17 |
| $BC_3F_3$ Line 8 | 0.19 |
| Large Sm Introgression Donor | 0.12 |
| Recurrent Parent 1 | 0.14 |
| Recurrent Parent 2 | 0.19 |
| Recurrent Parent 3 | 0.19 |

Example 3. Identification of TBRFV-Resistant Tomato Plants

A panel of 60 elite lines was tested for their performance against Tomato Brown Rugose Fruit Virus (TBRFV) infection. The following protocol was used to determine resistance. To prepare the inoculum for the experiment, a leaf infected with TBRFV showing clear mosaic symptoms was crushed with a small amount of water. The remaining leaf slurry was diluted to a concentration of 20 g leaf/100 mL water. A small amount of carborundum powder was added with a maximum of 1 tsp/L, however any other abrasive powder that is used in rub inoculation may be used. The inoculum suspension was kept on ice and in the dark until testing. The experiment contained control plants consisting of a resistant plant, e.g. FDR-I15-0403V, and a susceptible plant. The plants were grown in a randomized complete block design. Plants were inoculated with TBRFV 4 weeks after transplanting when the $2^{nd}$ truss is flowering. Prior to inoculation, the side shoots were trimmed so that only the main stem remained. A portion of the inoculum was placed on two fully expanded leaves between the $1^{st}$ and $2^{nd}$ truss. The leaves with inoculum were then gently rubbed to introduce the virus into the leaf. TBRFV infection was first evaluated one month after infection and again two months after infection, when the plants had six trusses. During the evaluations, leaf, fruit spot, and fruit necrosis symptoms were measured on a 1-9 scale, where a 1 indicated a complete absence of symptoms and a 9 indicated complete susceptibility. The experiment was deemed successful if 90% of the controls performed as expected for one of the symptoms.

The level of fruit symptoms and leaf symptoms was determined separately. From this analysis it was found that one proprietary elite inbred line provided high levels of resistance against both fruit and leaf symptoms. This line was further used to map the genetic region conferring the resistance against TBRFV.

In a further screen, 156 elite tomato lines relevant for the market segments in Jordan, Israel, Turkey, and Mexico were screened for resistance against TBRFV to find potential further resistance donors and shorten the breeding process by working with material that is adapted to the relevant market. In this screen, a strong correlation between high resistance against TBRFV and the presence of a *Stemphylium* resistance introgression on chromosome 11 was observed. This relationship is confirmed by the genetic experiments of the TBRFV locus in the following example.

Example 4. Mapping TBRFV Resistance in Tomato

The proprietary elite inbred line identified as showing high levels of resistance against both fruit and leaf symptoms in Example 3 was used for further mapping. This line was crossed to two different susceptible tomato lines and the $F_2$ progeny of each of these crosses was genotyped and phenotyped based on TBRFV resistance. In the subsequent QTL analysis for both populations, a QTL region conferring TBRFV resistance was found on chromosome 11. In addition, it was found that the resistance is recessive.

Further fine-mapping was done by selecting $F_3$ lines that segregated for the QTL interval on chromosome 11. From the subsequent $F_4$ generation, 35 lines were selected with a fixed recombination event in the QTL region. These lines were phenotyped for TBRFV resistance and genotyped with markers across the earlier found QTL region on chromosome 11. This set of markers included markers M1, M2, and M3. In the subsequent QTL analysis, it was found that the region conferring TBRFV resistance overlapped with the *Stemphylium* resistance locus on chromosome 11. Specifically, the QTL for TBRFV resistance was mapped between marker loci M1 and M3, where marker M2 could be used as a trait linked marker. To confirm that the *Stemphylium* resistance breeding event described in Example 2 above also conferred resistance to TBRFV, the event donor FDR-I15-0403V was tested for TBRFV resistance. It was found that this donor, which contains a different genetic background than the mapping population, also is highly resistant to TBRFV. Additional markers in the region between marker loci M1 and M3 were developed for further fine-mapping and selection of the trait (Table 3). Additional markers that can be used to select for the TBRFV resistance trait are: M4, a SNP marker with a [T/G] change at 8,891,489 bp on chromosome 11 of the public tomato genome map version SL2.50; M5, a SNP marker with a [C/T] change at 9,355,794 bp on chromosome 11 of the public tomato genome map version SL2.50; M6, a SNP marker with a [A/T] change at 9,401,319 bp on chromosome 11 of the public tomato genome map version SL2.50; M7, a SNP marker with a [G/T] change at 9,406,414 bp on chromosome 11 of the public tomato genome map version SL2.50; M8, a SNP marker with a [A/T] change at 9,421,426 bp on chromosome 11 of the public tomato genome map version SL2.50; M9, a SNP marker with a [T/C] change at 9,470,789 bp on chromosome 11 of the public tomato genome map version SL2.50; and M10, a SNP marker with a [A/G] change at 9,756,371 bp on chromosome 11 of the public tomato genome map version SL2.50. Markers M4, M5, M6, M7, M8, M9, and M10 may also be used to select for the reduced introgression conferring *Stemphylium* resistance.

TABLE 3

List of markers and favorable alleles at each marker for tracking resistance QTLs.

| Marker name | Chr. | Genetic Position (cM) | Public position SNP (bp) | Marker size (bp) | SNP position in marker (bp) | SNP change | Favorable allele | Marker sequence (SEQ ID NO) | Fwd primer (SEQ ID NO) | Rev primer (SEQ ID NO) | Probe 1 (SEQ ID NO) | Probe 2 (SEQ ID NO) |
|---|---|---|---|---|---|---|---|---|---|---|---|---|
| M1 | 11 | 34.35 | 8,894,829 | 1213 | 529 | [A/C] | A | 1 | | | | |
| M4 | 11 | 34.64 | 8,891,489 | 101 | 51 | [T/G] | G | 4 | 5 | 6 | 7 | 8 |
| M5 | 11 | 35.25 | 9,355,794 | 201 | 101 | [C/T] | T | 9 | | | | |
| M6 | 11 | 35.35 | 9,401,319 | 201 | 101 | [A/T] | T | 10 | 11 | 12 | 13 | 14 |
| M7 | 11 | 35.36 | 9,406,414 | 201 | 101 | [G/T] | T | 15 | 16 | 17 | 18 | 19 |
| M8 | 11 | 35.39 | 9,421,426 | 201 | 101 | [A/T] | T | 20 | 21 | 22 | 23 | 24 |
| M9 | 11 | 35.48 | 9,470,789 | 187 | 101 | [T/C] | C | 25 | 26 | 27 | 28 | 29 |
| M2 | 11 | 35.7 | 9,591,834 | 199 | 99 | [G/A] | A | 2 | | | | |
| M10 | 11 | 36.01 | 9,756,371 | 184 | 101 | [A/G] | G | 30 | 31 | 32 | 33 | 34 |
| M3 | 11 | 36.15 | 9,826,973 | 1968 | 787 | [A/T] | A | 3 | | | | |

What is claimed is:

1. A *Solanum lycopersicum* plant comprising a recombinant chromosomal segment on chromosome 11, wherein said chromosomal segment comprises a *Solanum lycopersicum* allele at marker locus M1 (SEQ ID NO:1) and an *Solanum pimpinellifolium* allele at marker locus M2 (SEQ ID NO:2), wherein said chromosomal segment comprises a *Stemphylium* resistance allele from *Solanum pimpinellifolium* conferring increased resistance to *Stemphylium* to said plant compared to a plant not comprising said allele, and wherein the chromosomal segment lacks a deleterious allele genetically linked to said *Stemphylium* resistance allele that confers small fruit size when present.

2. The plant of claim 1, wherein said *Stemphylium* resistance allele is further defined as:
   (a) located within a chromosomal segment on chromosome 11 flanked by marker locus M1 (SEQ ID NO:1) and marker locus M3 (SEQ ID NO:3) in said plant; or
   (b) within a chromosomal segment on chromosome 11 comprising a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30) in said plant.

3. The plant of claim 1, wherein said plant further comprises a *Solanum lycopersicum* allele at marker locus M3 (SEQ ID NO:3).

4. The plant of claim 1, wherein a representative sample of seed comprising said chromosomal segment has been deposited under NCMA Accession No. 202103011.

5. The plant of claim 1, wherein said recombinant chromosomal segment further comprises a Tomato Brown Rugose Fruit Virus (TBRFV) resistance allele.

6. The plant of claim 5, wherein said TBRFV resistance allele is located within a chromosomal segment flanked by marker locus M1 (SEQ ID NO:1) and marker locus M3 (SEQ ID NO:3) on chromosome 11 in said plant.

7. The plant of claim 6, wherein said plant is homozygous for said TBRFV resistance allele.

8. A cell, seed, or plant part of the plant of claim 1, wherein the cell, seed, or plant part comprises said recombinant chromosomal segment.

9. The cell, seed, or plant part of claim 8, wherein a representative sample of seed comprising said chromosomal segment has been deposited under NCMA Accession No. 202103011.

10. The cell, seed, or plant part of claim 8, further defined as a seed.

11. A recombinant DNA segment comprising a *Stemphylium* resistance allele from *Solanum pimpinellifolium* that confers to a *Solanum lycopersicum* plant increased resistance to *Stemphylium* and lacking a deleterious allele genetically linked thereto that confers small fruit size wherein said DNA segment comprises DNA from *Solanum lycopersicum* at marker locus M1 (SEQ ID NO:1) and *Solanum pimpinellifolium* DNA at marker locus M2 (SEQ ID NO:2), and wherein a representative sample of seed comprising said DNA segment has been deposited under NCMA Accession No. 202103011.

12. The recombinant DNA segment of claim 11, wherein said recombinant DNA segment comprises a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30).

13. The recombinant DNA segment of claim 11, further defined as comprised within a plant, plant part, plant cell, or seed.

14. The recombinant DNA segment of claim 13, wherein said DNA segment confers to said plant increased resistance to *Stemphylium*.

15. A method of producing a tomato plant exhibiting resistance to *Stemphylium*, comprising introgressing into a plant a *Stemphylium* resistance allele from *Solanum pimpinellifolium* within a recombinant chromosomal segment flanked in the genome of said plant by:
   marker locus M1 (SEQ ID NO:1) and marker locus M3 (SEQ ID NO:3) on chromosome 11;
   wherein said introgressed *Stemphylium* resistance allele confers to said plant increased resistance to *Stemphylium* compared to a plant not comprising said allele, and wherein said recombinant chromosomal segment lacks a deleterious allele genetically linked to said *Stemphylium* resistance allele that confers a small fruit size trait to said plant when present.

16. The method of claim 15, wherein said introgressed *Stemphylium* resistance allele is within a recombinant chromosomal segment on chromosome 11 comprising a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30).

17. The method of claim 16, wherein said recombinant chromosomal segment is defined by:
   a) a non-introgressed allele at marker locus M1 (SEQ ID NO:1);
   b) an introgressed allele at a marker locus selected from the group consisting of marker locus M2 (SEQ ID NO:2), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30); and
   c) a non-introgressed allele at marker locus M3 (SEQ ID NO:3).

18. The method of claim 15, wherein said introgressing comprises backcrossing, marker-assisted selection, or assaying for said *Stemphylium* resistance.

19. A tomato plant produced by the method of claim 15, wherein said plant comprises said *Stemphylium* resistance allele.

20. A method of selecting a tomato plant exhibiting resistance to *Stemphylium*, comprising:
   a) crossing the tomato plant of claim 1 with itself or with a second tomato plant of a different genotype to produce one or more progeny plants; and
   b) selecting a progeny plant comprising said *Stemphylium* resistance allele.

21. The method of claim 20, wherein selecting said progeny plant comprises detecting a marker locus genetically linked to said *Stemphylium* resistance allele.

22. The method of claim 21, wherein selecting said progeny plant comprises:
   (a) detecting a marker locus within or genetically linked to a chromosomal segment flanked in the genome of said plant marker locus M1 (SEQ ID NO:1) and marker locus M3 (SEQ ID NO:3) on chromosome 11; or
   (b) detecting at least one polymorphism at a locus selected from the group consisting of marker locus M1 (SEQ ID NO:1), marker locus M2 (SEQ ID NO:2), marker locus M3 (SEQ ID NO:3), marker locus M4 (SEQ ID NO:4), marker locus M5 (SEQ ID NO:9), marker locus M6 (SEQ ID NO:10), marker locus M7 (SEQ ID NO:15), marker locus M8 (SEQ ID NO:20), marker locus M9 (SEQ ID NO:25), and marker locus M10 (SEQ ID NO:30).

23. The method of claim 20, wherein said progeny plant is an $F_2$-$F_6$ progeny plant.

24. The method of claim 20, wherein producing said progeny plant comprises backcrossing.

\* \* \* \* \*

UNITED STATES PATENT AND TRADEMARK OFFICE
CERTIFICATE OF CORRECTION

PATENT NO. : 11,162,110 B2
APPLICATION NO. : 16/516032
DATED : November 2, 2021
INVENTOR(S) : Anton P. Allersma et al.

Page 1 of 1

It is certified that error appears in the above-identified patent and that said Letters Patent is hereby corrected as shown below:

On the Title Page

Item (73) delete "Seminis Vegatable Seeds, Inc." and insert --Seminis Vegetable Seeds, Inc.--

Signed and Sealed this
Twelfth Day of December, 2023

Katherine Kelly Vidal
*Director of the United States Patent and Trademark Office*